US010859570B2

(12) United States Patent
Choi

(10) Patent No.: US 10,859,570 B2
(45) Date of Patent: Dec. 8, 2020

(54) METHODS FOR DETECTING AN ANALYTE USING AN ANALYTE DETECTION DEVICE

(71) Applicants: GANGNEUNG-WONJU NATIONAL UNIVERSITY INDUSTRY ACADEMY COOPERATION GROUP, Gangwon-do (KR); AMOLIFESCIENCE CO., LTD., Seoul (KR)

(72) Inventor: Suk-Jung Choi, Gangwon-do (KR)

(73) Assignees: GANGNEUNG-WONJU NATIONAL UNIVERSITY INDUSTRY ACADEMY COOPERATION GROUP; AMOLIFESCIENCE Co., Ltd.

( * ) Notice: Subject to any disclaimer, the term of this patent is extended or adjusted under 35 U.S.C. 154(b) by 165 days.

(21) Appl. No.: 15/785,272

(22) Filed: Oct. 16, 2017

(65) Prior Publication Data
US 2018/0038854 A1 Feb. 8, 2018

Related U.S. Application Data

(62) Division of application No. 14/915,206, filed as application No. PCT/KR2014/007976 on Aug. 27, 2014, now abandoned.

(30) Foreign Application Priority Data

Aug. 29, 2013 (KR) .................. 10-2013-0102944
Dec. 30, 2013 (KR) .................. 10-2013-0166909

(51) Int. Cl.
*G01N 33/553* (2006.01)
*G01N 33/543* (2006.01)
(Continued)

(52) U.S. Cl.
CPC ........ *G01N 33/54326* (2013.01); *B01L 3/502* (2013.01); *B01L 3/502761* (2013.01);
(Continued)

(58) Field of Classification Search
CPC ....... B01L 3/502761; B01L 2200/0647; B01L 2200/0668; B01L 2200/0673;
(Continued)

(56) References Cited

U.S. PATENT DOCUMENTS 5,945,281 A * 8/1999 Prabhu .............. B01L 3/502761
435/287.1
7,776,532 B2 8/2010 Gibson et al.
(Continued)

FOREIGN PATENT DOCUMENTS

CN 101149376 3/2008
CN 101301632 11/2008
(Continued)

OTHER PUBLICATIONS

"Ficoll", 2016. In Wikipedia. Retrieved Jun. 19, 2017, from https://en.wikipedia.org/wiki/Ficoll.
(Continued)

*Primary Examiner* — Christopher L Chin
(74) *Attorney, Agent, or Firm* — Wells St. John P.S.

(57) ABSTRACT

The present invention relates to an analyte detection device comprising: a sample chamber for storing a mixture solution of a sample comprising an analyte and a reactant comprising particles; a detection chamber for storing a detection solution; and a channel placed between the sample chamber and the detection chamber to prevent the mixture solution and the detection solution from being mixed with each other, the analyte detection device characterized by detecting the analyte by moving the particles from the sample chamber to the detection chamber using moving means.

3 Claims, 32 Drawing Sheets

(51) Int. Cl.
*G01N 35/00* (2006.01)
*B01L 3/00* (2006.01)
*B03C 1/01* (2006.01)
*B03C 1/28* (2006.01)

(52) U.S. Cl.
CPC .............. *B03C 1/01* (2013.01); *B03C 1/288* (2013.01); *G01N 33/54386* (2013.01); *G01N 33/54393* (2013.01); *G01N 35/00* (2013.01); *B01L 2200/0647* (2013.01); *B01L 2200/0668* (2013.01); *B01L 2200/0673* (2013.01); *B01L 2200/141* (2013.01); *B01L 2300/06* (2013.01); *B01L 2300/0627* (2013.01); *B01L 2300/0803* (2013.01); *B01L 2300/0864* (2013.01); *B01L 2300/0877* (2013.01); *B01L 2300/12* (2013.01); *B01L 2400/043* (2013.01); *B01L 2400/0409* (2013.01); *B01L 2400/0457* (2013.01); *B01L 2400/0481* (2013.01); *B03C 2201/18* (2013.01); *B03C 2201/26* (2013.01); *G01N 2035/00158* (2013.01)

(58) Field of Classification Search
CPC ..... B01L 2300/0803; B01L 2300/0864; B01L 2400/0409; B01L 2400/043; B01L 2400/0457; B01L 2400/0481; B01L 3/502; B01L 2200/141; B01L 2300/06; B01L 2300/0627; B01L 2300/0877; B01L 2300/12; B03C 1/01; B03C 1/288; B03C 2201/18; B03C 2201/26; G01N 35/00; G01N 2035/00158; G01N 33/54326; G01N 33/54386; G01N 33/54393
USPC ....................................................... 435/288.5
See application file for complete search history.

(56) References Cited

U.S. PATENT DOCUMENTS

| | | | |
|---|---|---|---|
| 7,927,561 B2 * | 4/2011 | Kirakossian | B01L 3/508 422/400 |
| 7,951,560 B2 | 5/2011 | Myette et al. | |
| 7,998,696 B2 | 8/2011 | Zaugg et al. | |
| 8,114,538 B2 | 2/2012 | Agnew et al. | |
| 8,178,704 B2 | 5/2012 | Bazin et al. | |
| 8,241,852 B2 | 8/2012 | Yue et al. | |
| 8,304,203 B2 | 11/2012 | Zaugg et al. | |
| 8,444,991 B2 | 5/2013 | Randolph et al. | |
| 8,530,481 B2 | 9/2013 | Lin et al. | |
| 8,765,391 B2 | 7/2014 | Zaugg et al. | |
| 8,822,695 B2 | 9/2014 | Buller et al. | |
| 9,005,580 B2 | 4/2015 | Haraldsson et al. | |
| 9,005,910 B2 | 4/2015 | Ohiro et al. | |
| 9,040,561 B2 | 5/2015 | Dallwig et al. | |
| 9,163,279 B2 | 10/2015 | Wakeley et al. | |
| 9,187,729 B2 | 11/2015 | DePaz et al. | |
| 9,212,385 B2 | 12/2015 | Batchelor et al. | |
| 9,532,950 B2 | 1/2017 | Kusumoto et al. | |
| 9,631,176 B2 | 4/2017 | Yoshimura et al. | |
| 2006/0228734 A1 * | 10/2006 | Vann | B01L 3/5025 435/6.19 |
| 2009/0143250 A1 * | 6/2009 | Lee | B01L 3/502738 506/39 |
| 2009/0148869 A1 | 6/2009 | Zaugg et al. | |
| 2009/0221431 A1 | 9/2009 | Yoo | |
| 2010/0081213 A1 * | 4/2010 | Lee | B01L 3/502738 436/506 |
| 2010/0086925 A1 * | 4/2010 | Lee | B01L 3/5027 435/6.11 |
| 2010/0144558 A1 | 6/2010 | Zenhausern et al. | |
| 2010/0311085 A1 | 12/2010 | Zaugg et al. | |
| 2011/0207150 A1 | 8/2011 | Zaugg et al. | |
| 2011/0269151 A1 | 11/2011 | Kim | |
| 2012/0178182 A1 | 7/2012 | Kim et al. | |
| 2014/0212990 A1 * | 7/2014 | Nimri | G01N 33/54326 436/501 |

FOREIGN PATENT DOCUMENTS

| | | |
|---|---|---|
| CN | 102580644 | 7/2012 |
| CN | 102655938 | 9/2012 |
| CN | 201480058392.5 | 7/2017 |
| JP | 2011-506935 | 3/2011 |
| KR | 10-2011-0120790 | 11/2011 |
| KR | 10-1217572 | 1/2013 |

OTHER PUBLICATIONS

Decision on Appeal No. 2013-000274, before the USPTO Patent Trial and Appeal Board, dated Mar. 27, 2015 in U.S. Appl. No. 12/314,706, 6 pages.
Office Action dated Nov. 8, 2016, in Chinese Patent Appl No. 2014800583925—English Translation and Full Reference.

* cited by examiner

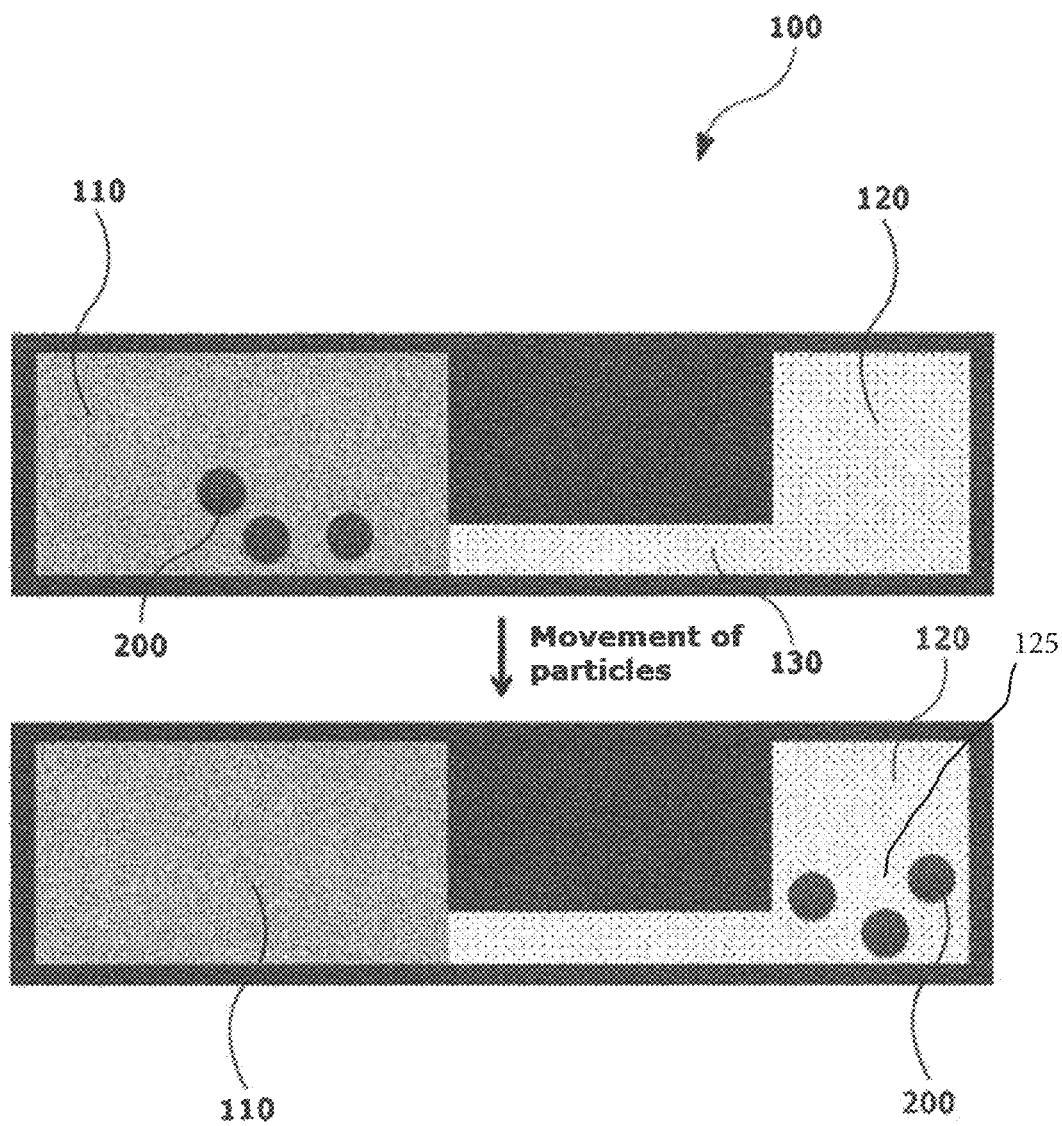
[FIG. 1]

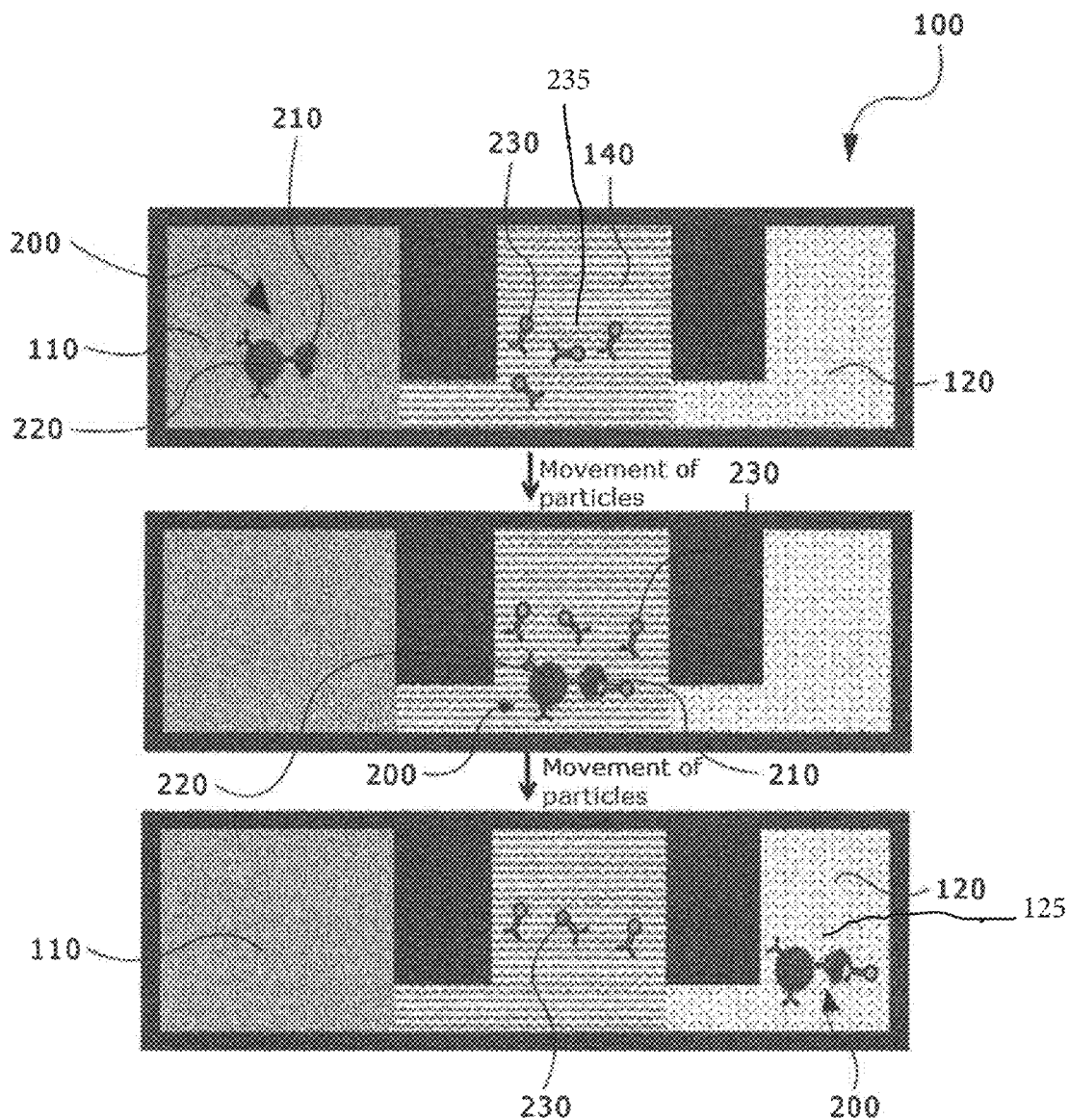
[FIG. 2]

[FIG. 3]
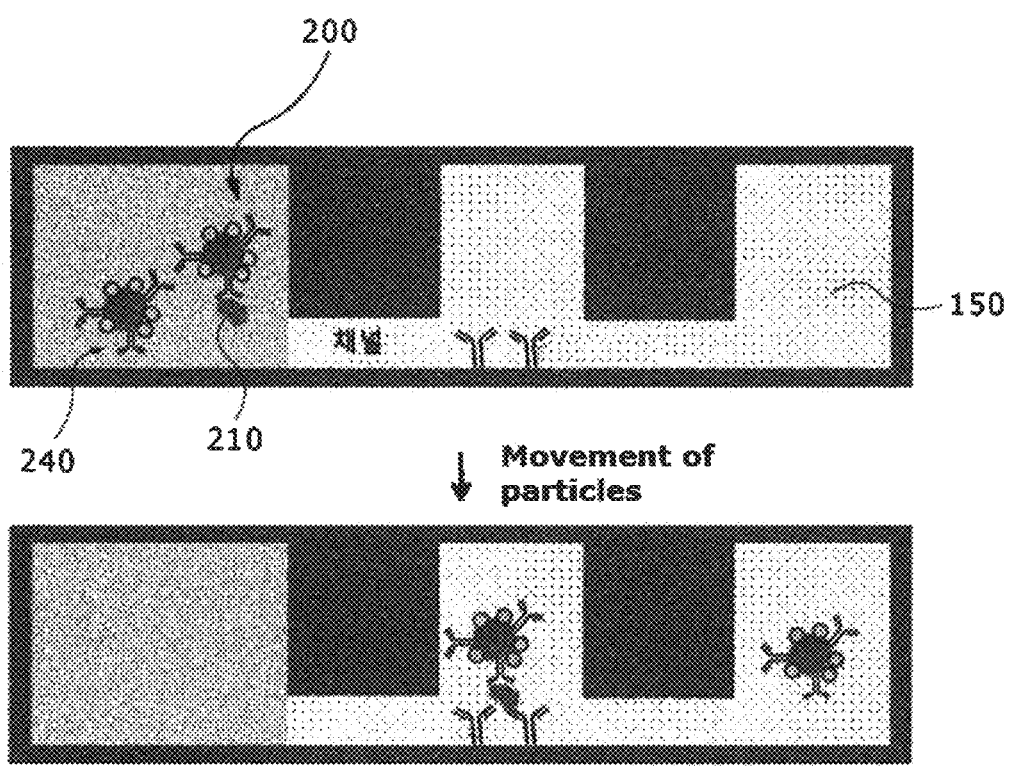

[FIG. 4]
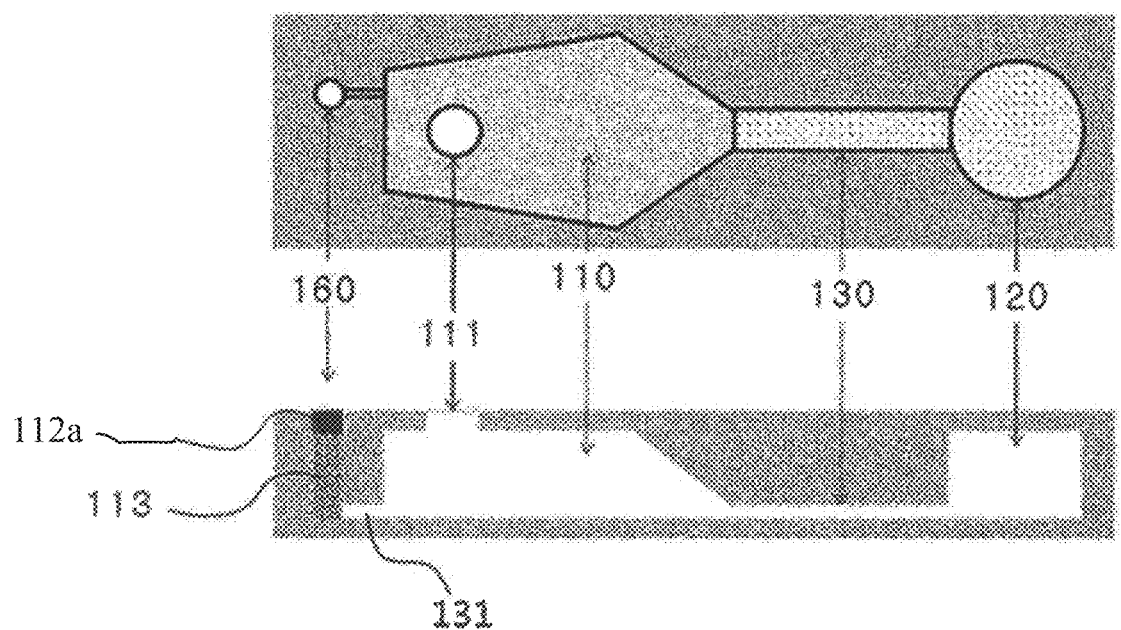

[FIG. 5]
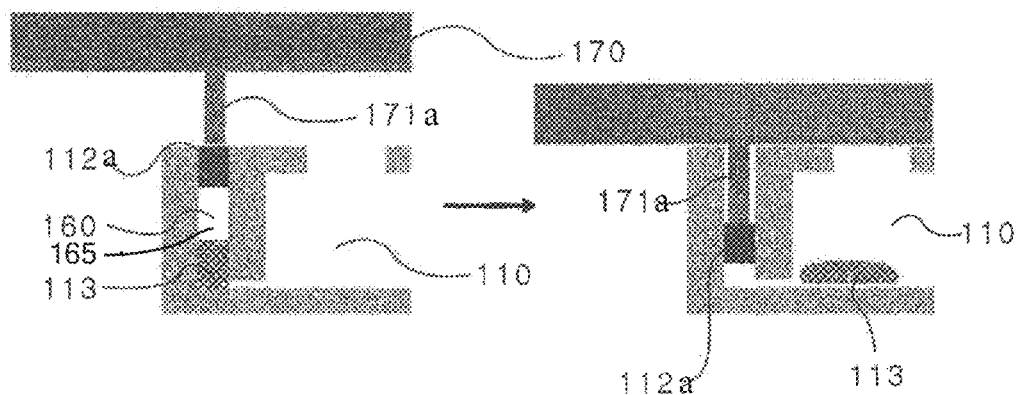
[FIG. 6]
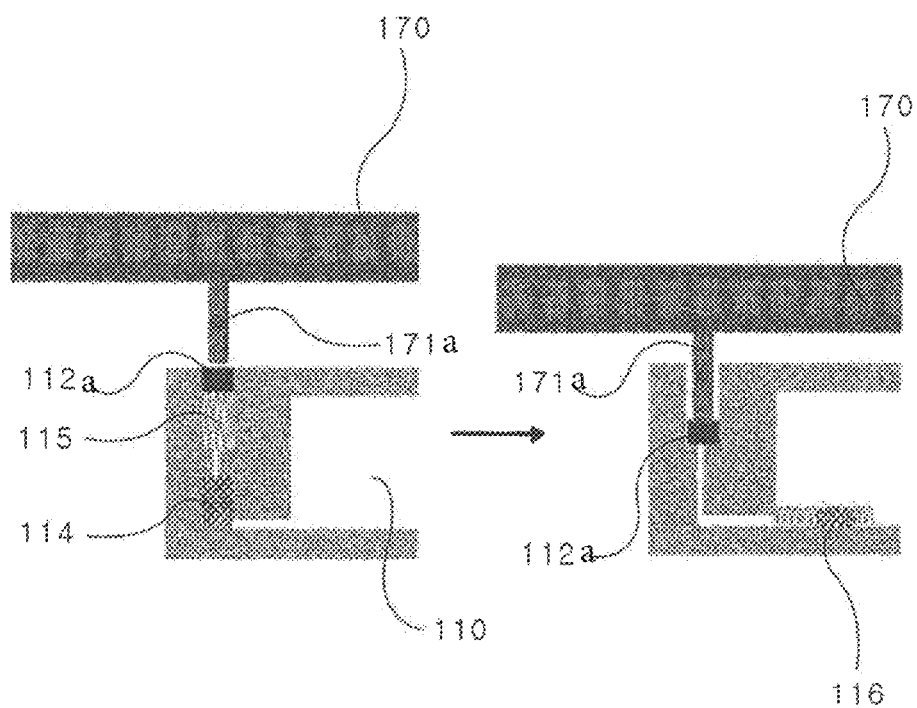

[FIG. 7]
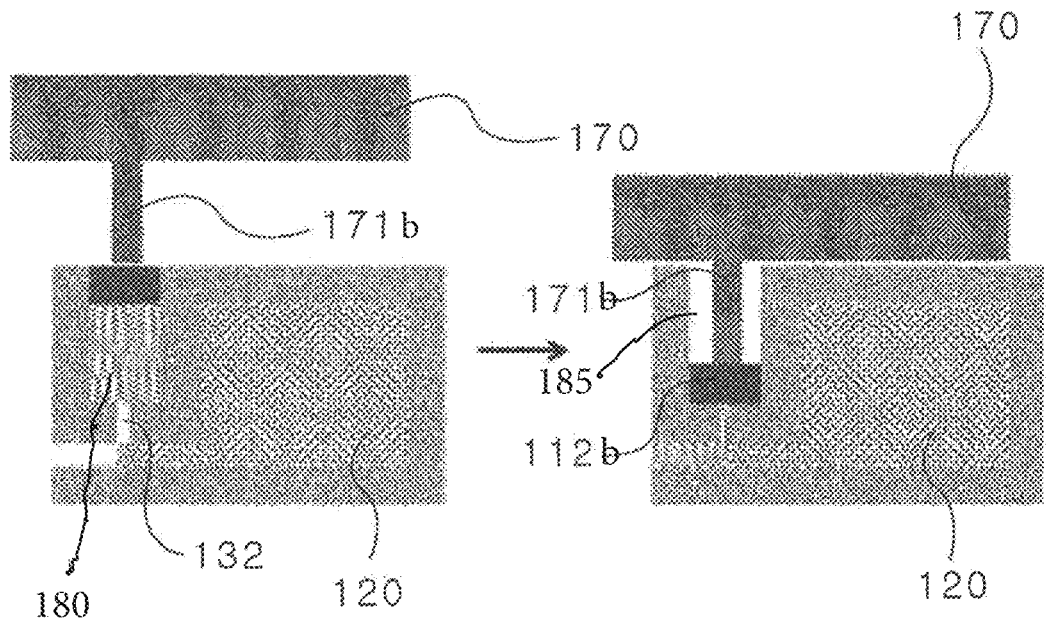
[FIG. 8]
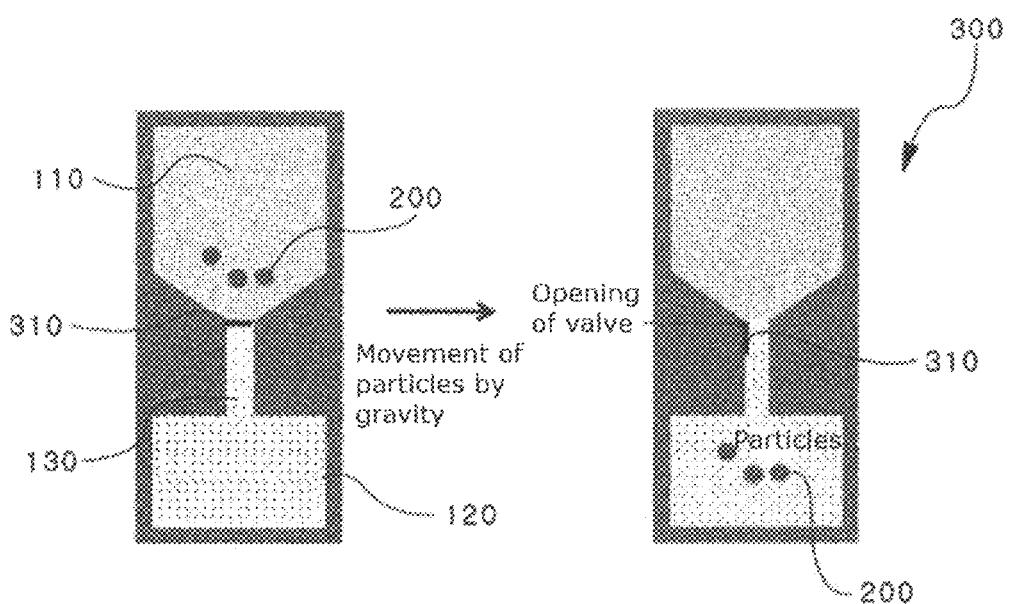

[FIG. 9]
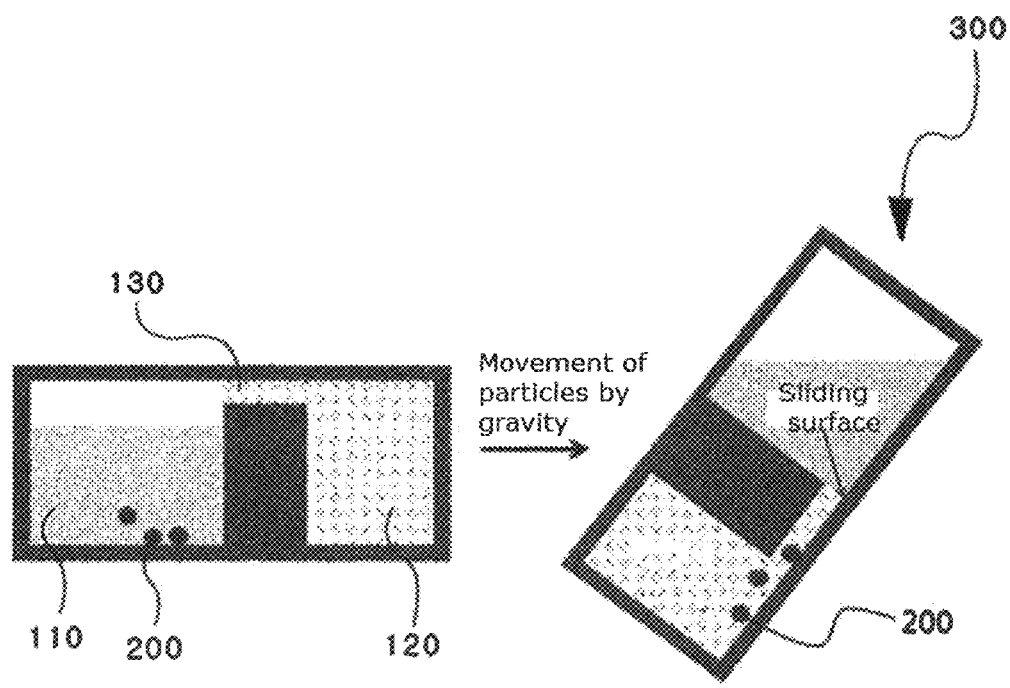

[FIG. 10]
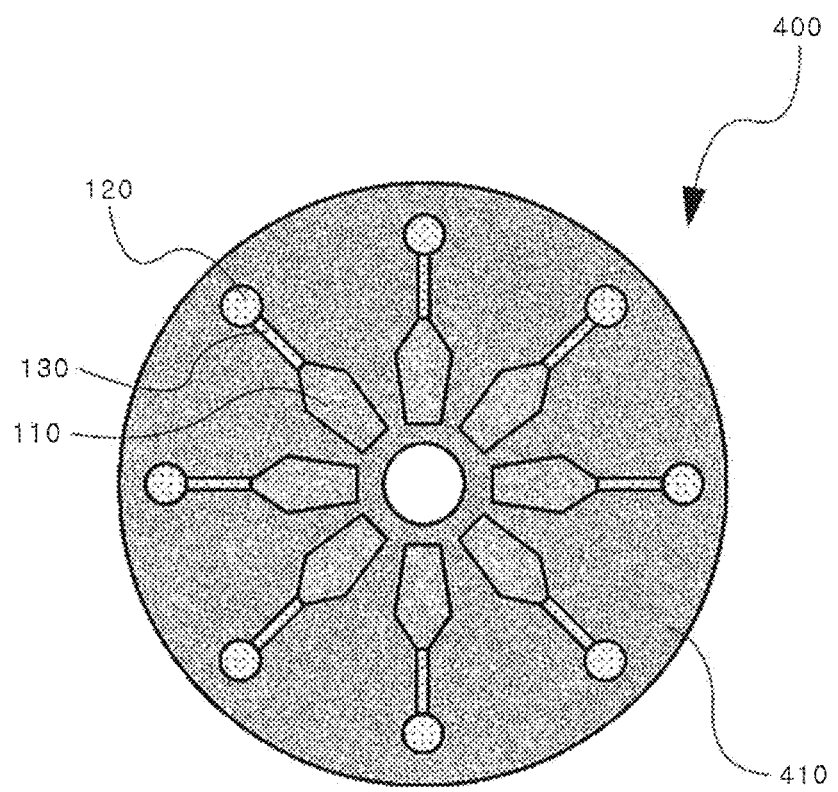

[FIG. 11]
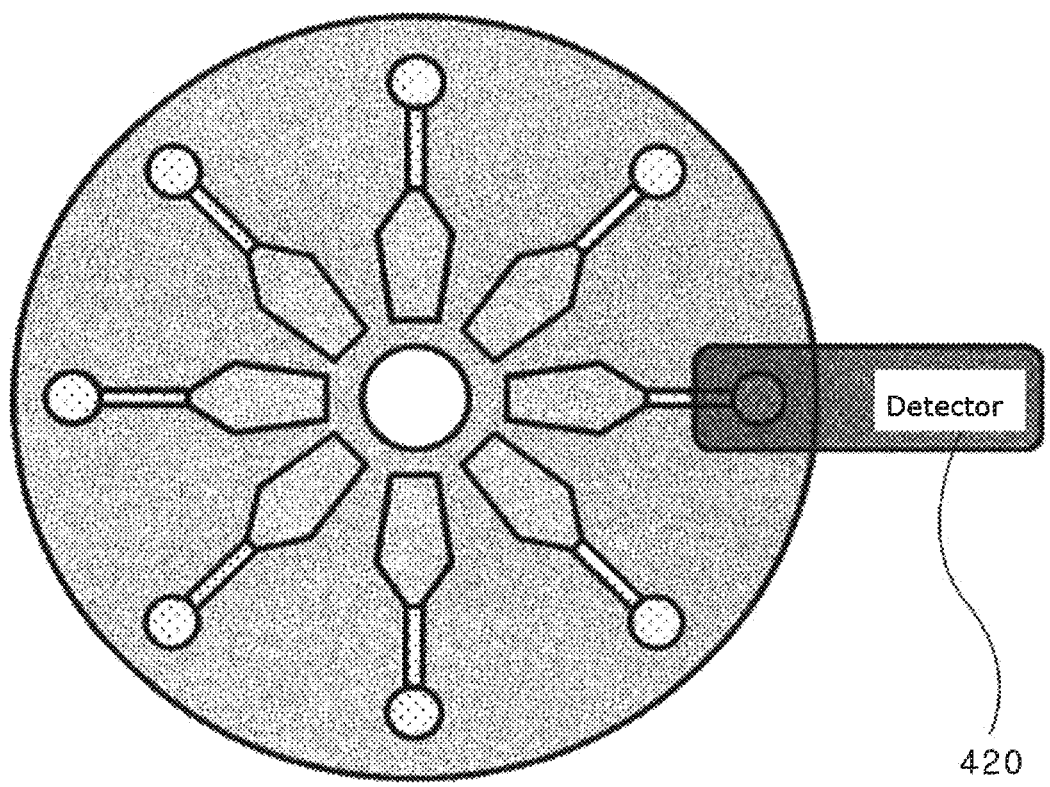

[FIG. 12]
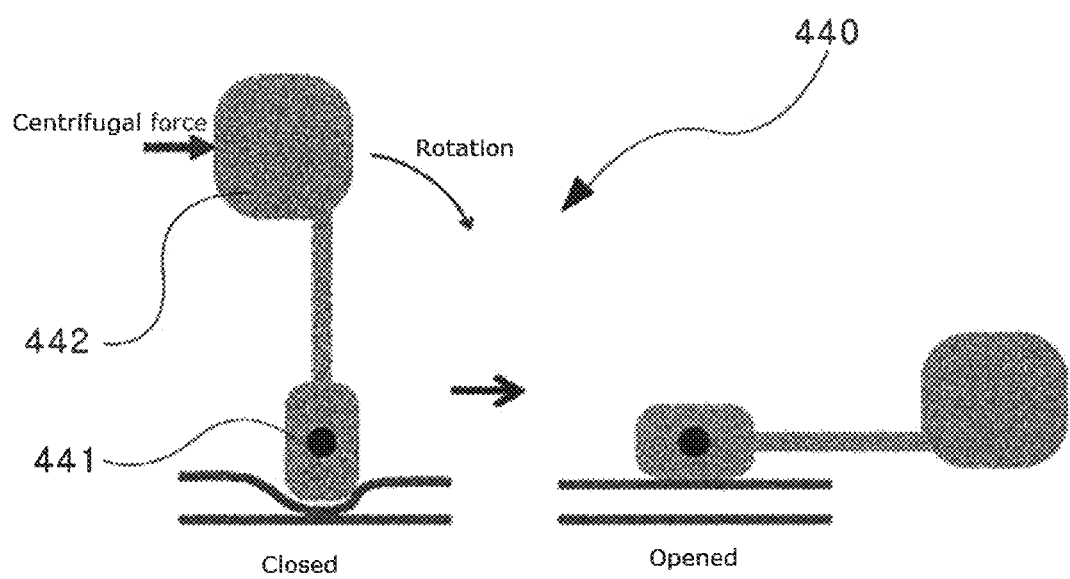

[FIG. 13]
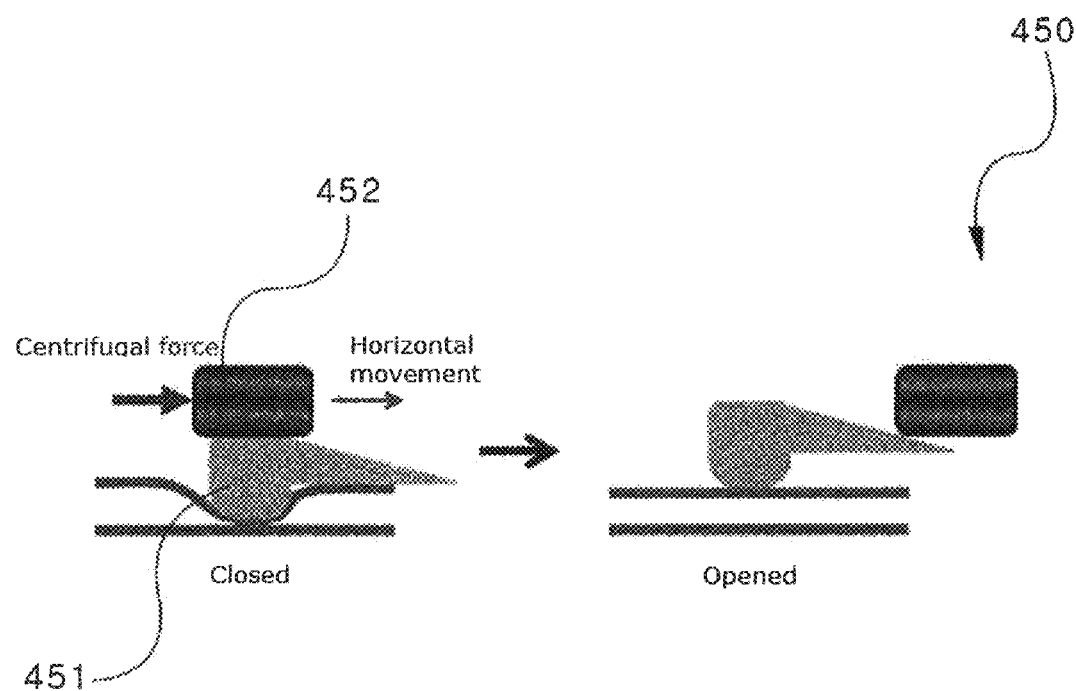

[FIG. 14]
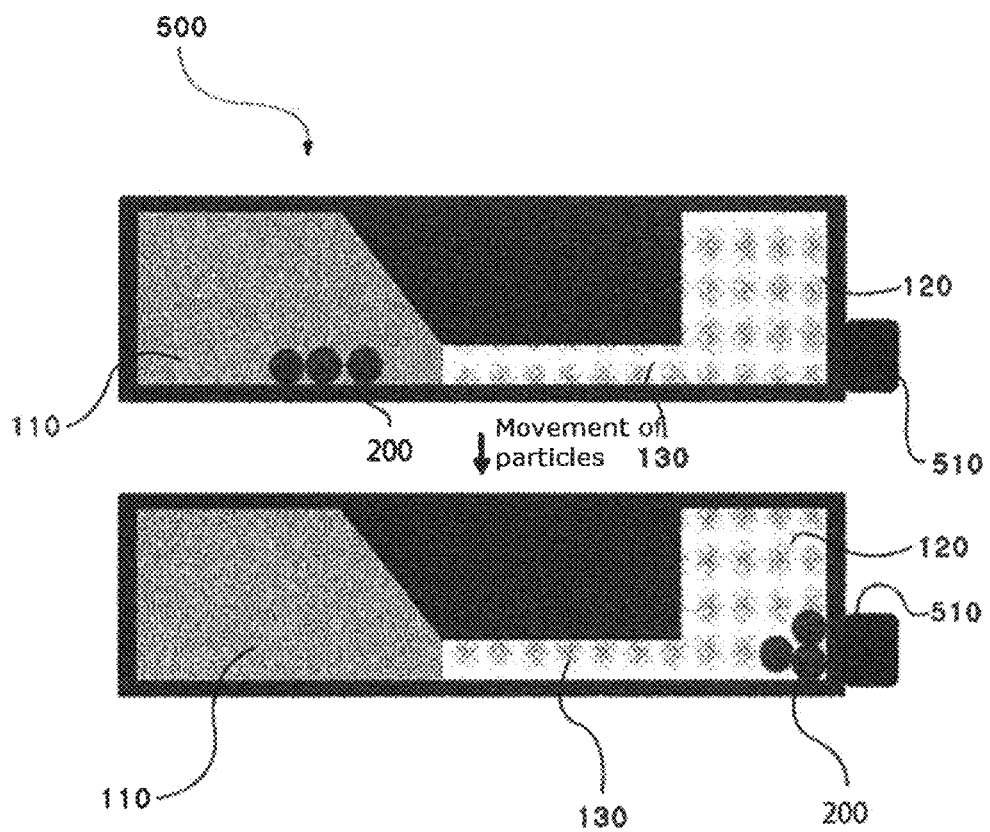

[FIG. 15]
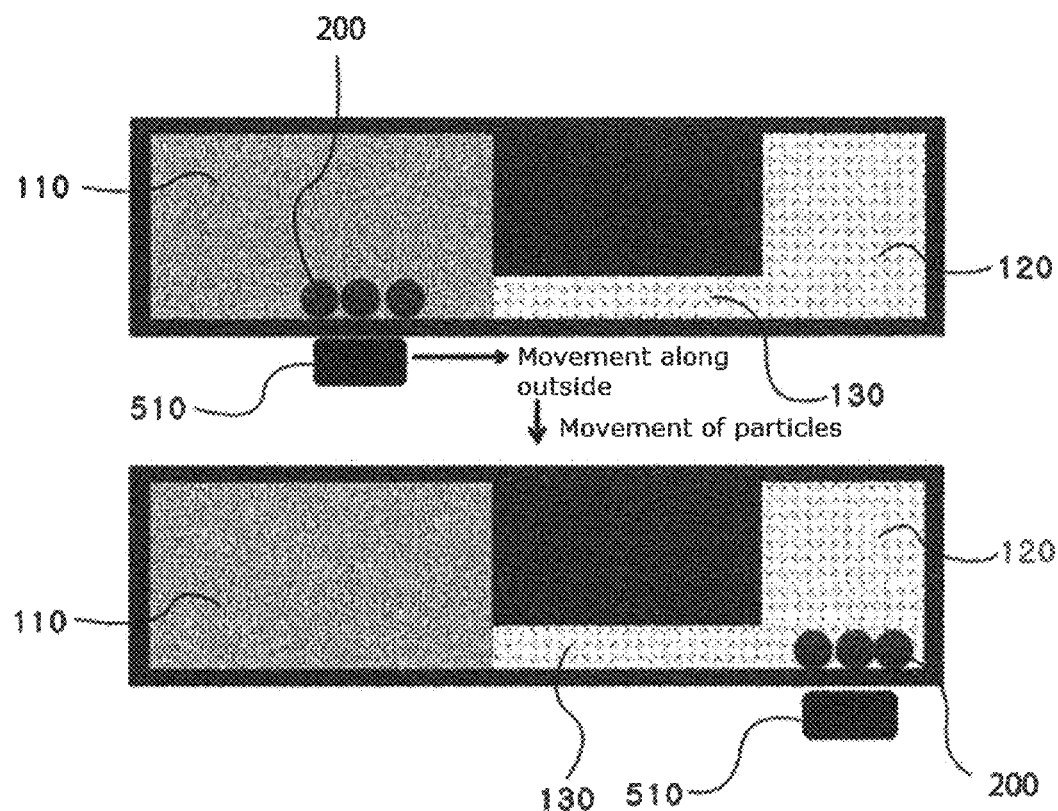

[FIG. 16]
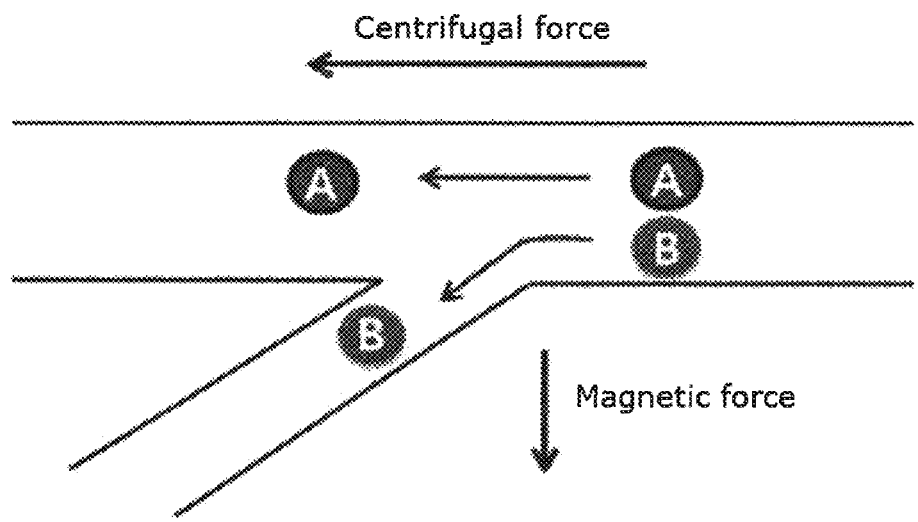

[FIG. 17]
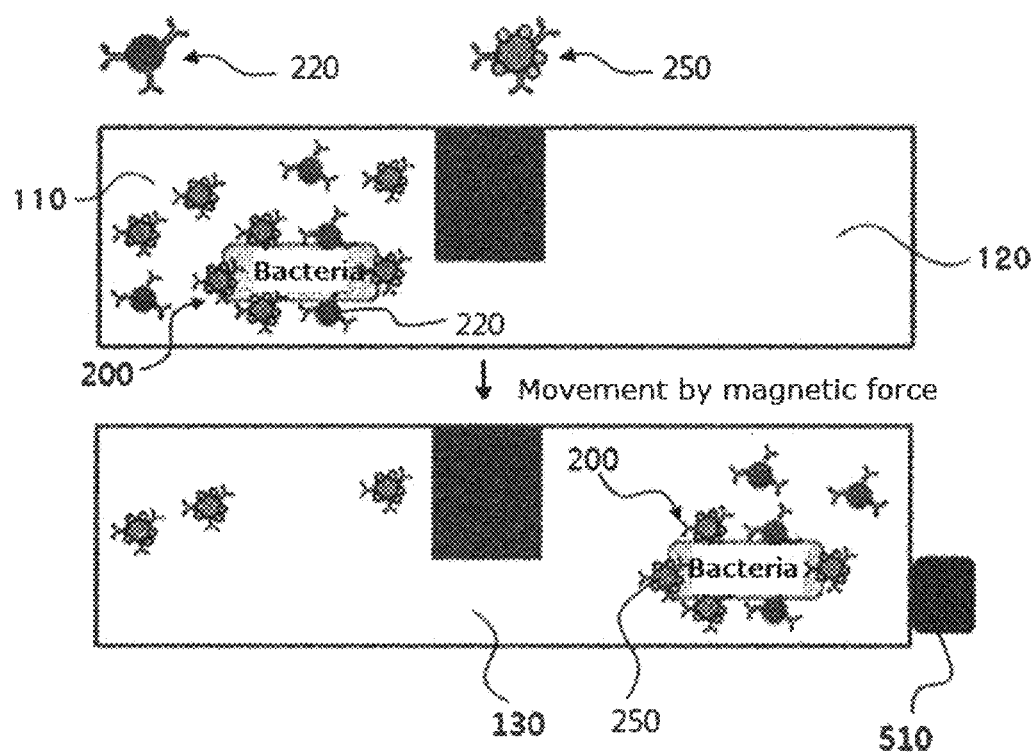

[FIG. 18]
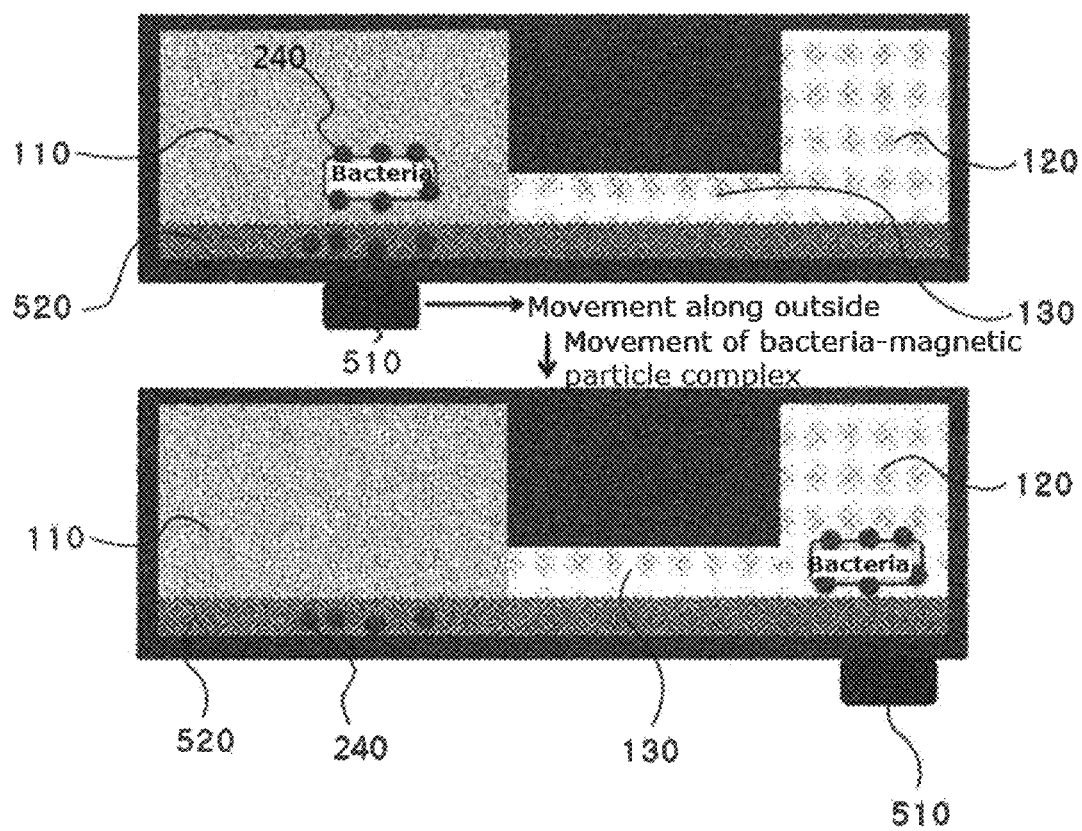

[FIG. 19]
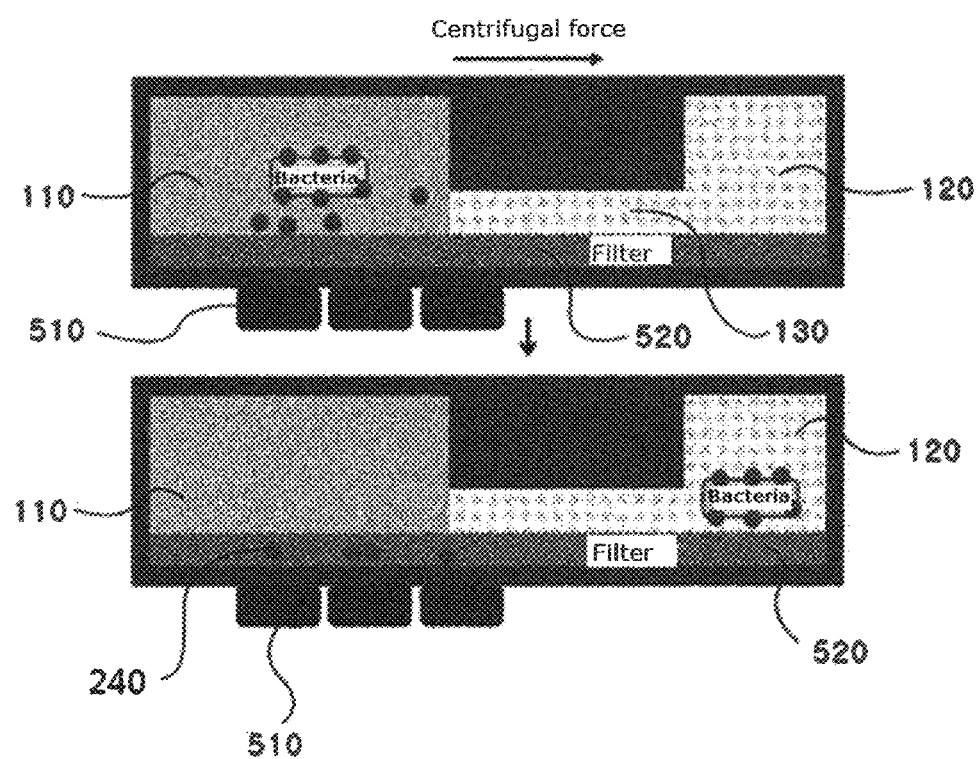

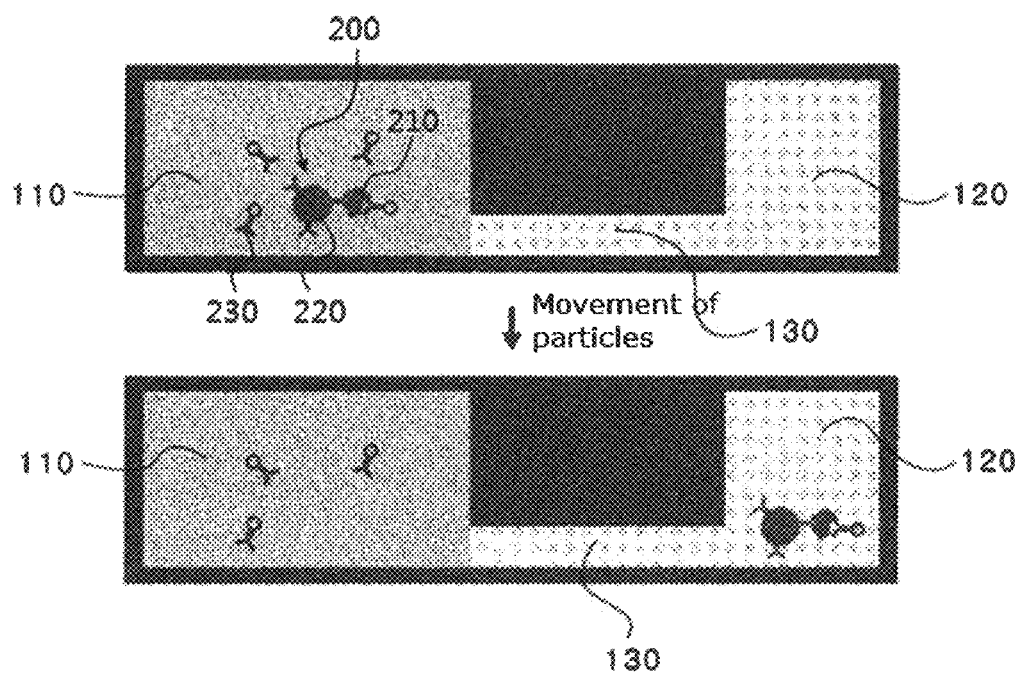
[FIG. 20]

[FIG. 21]
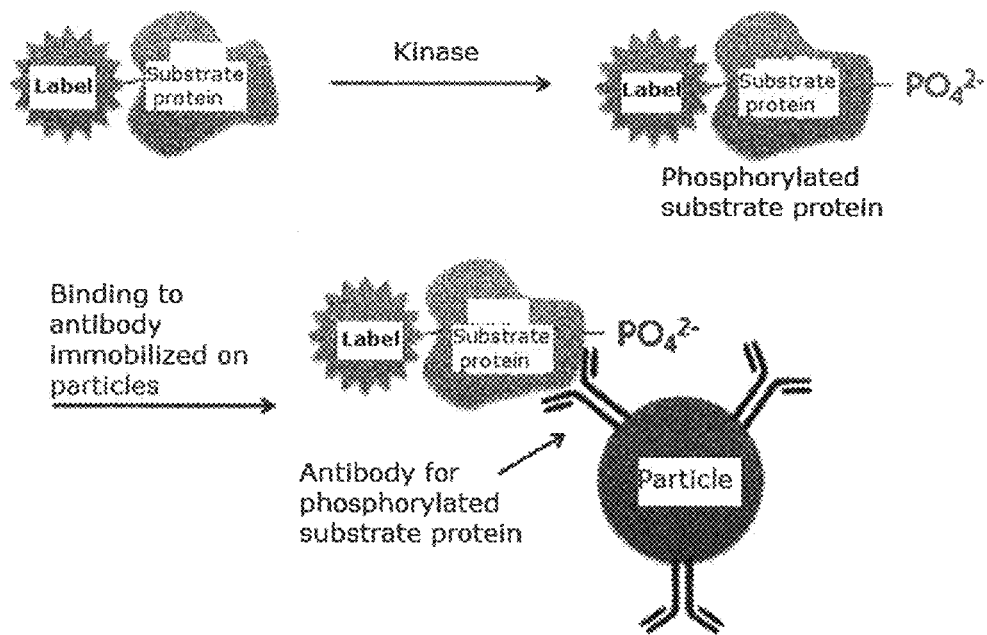

[FIG. 22]
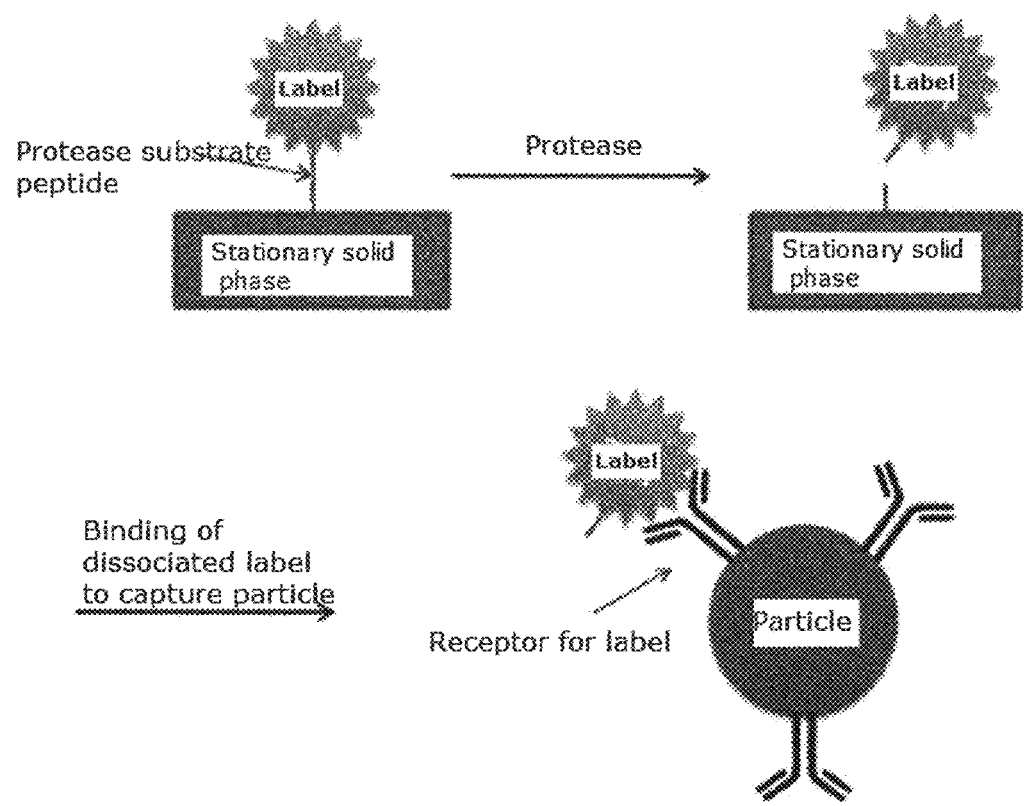

[FIG. 23]
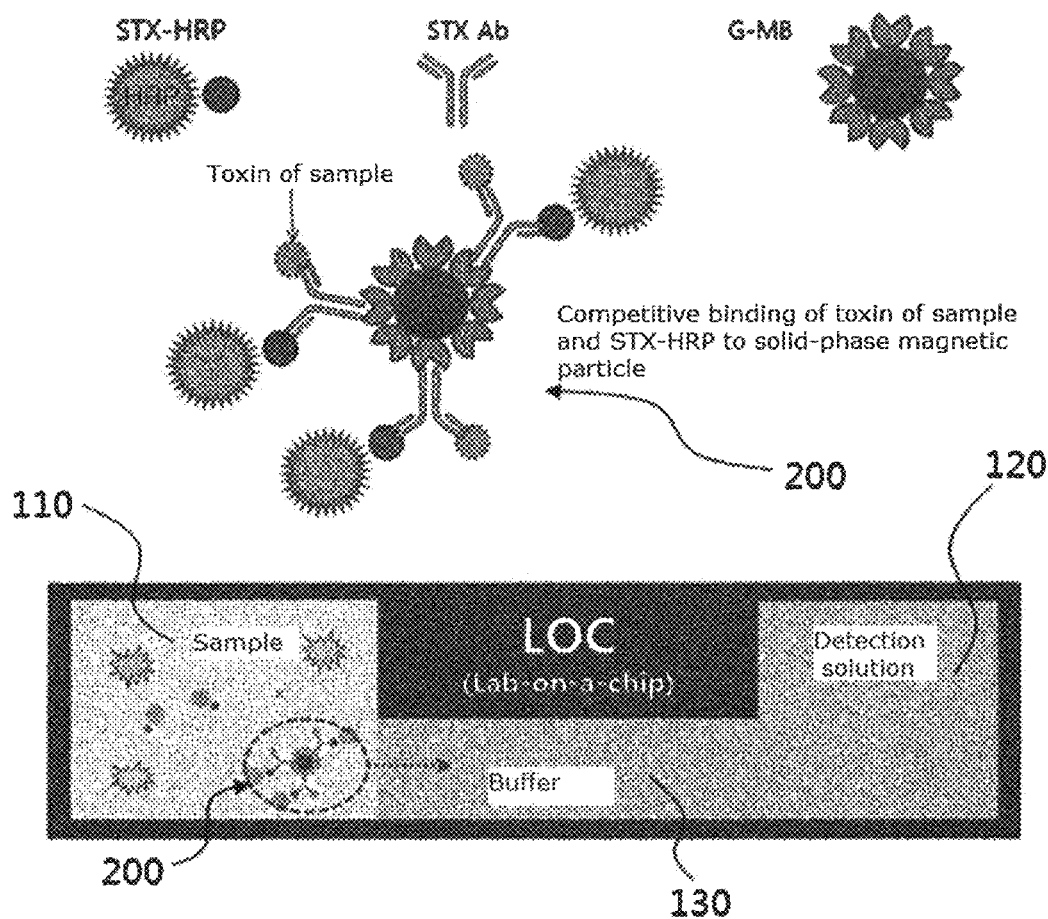

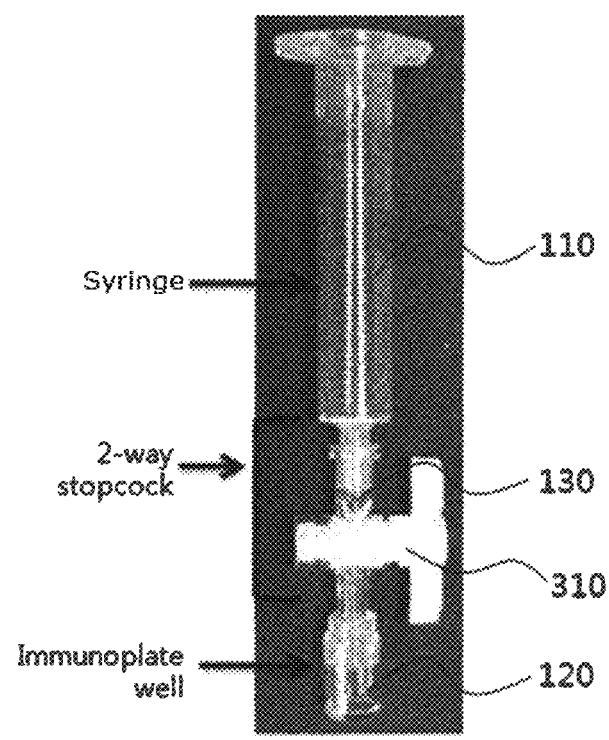
[FIG. 24]

[FIG. 25]

[FIG. 26]
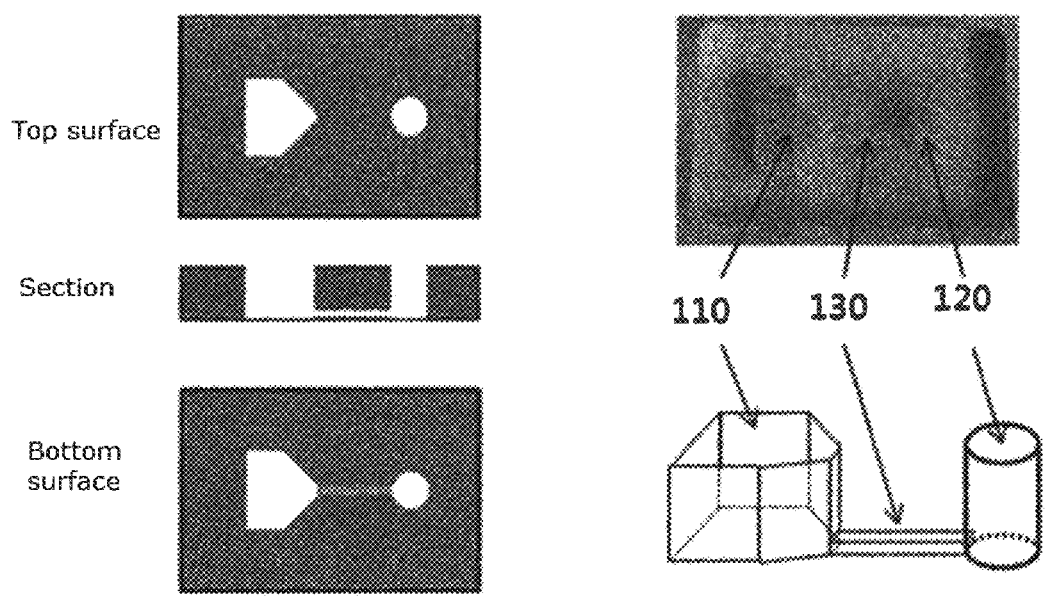

[FIG. 27A]
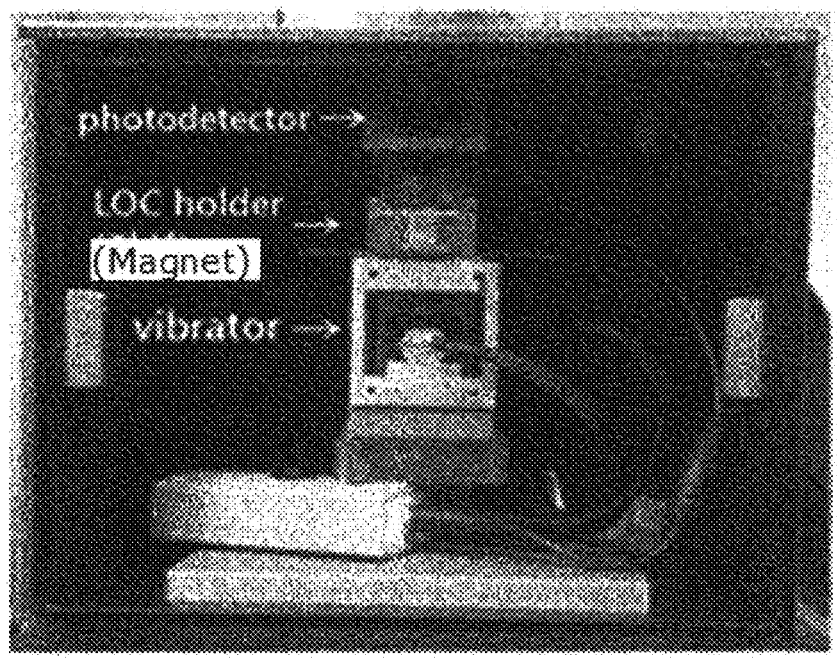

[FIG. 27B]
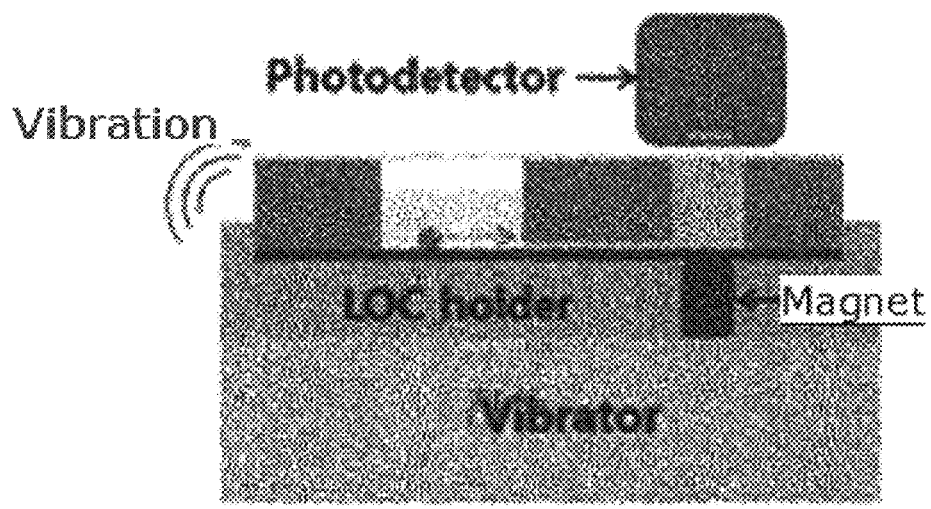

[FIG. 28A]
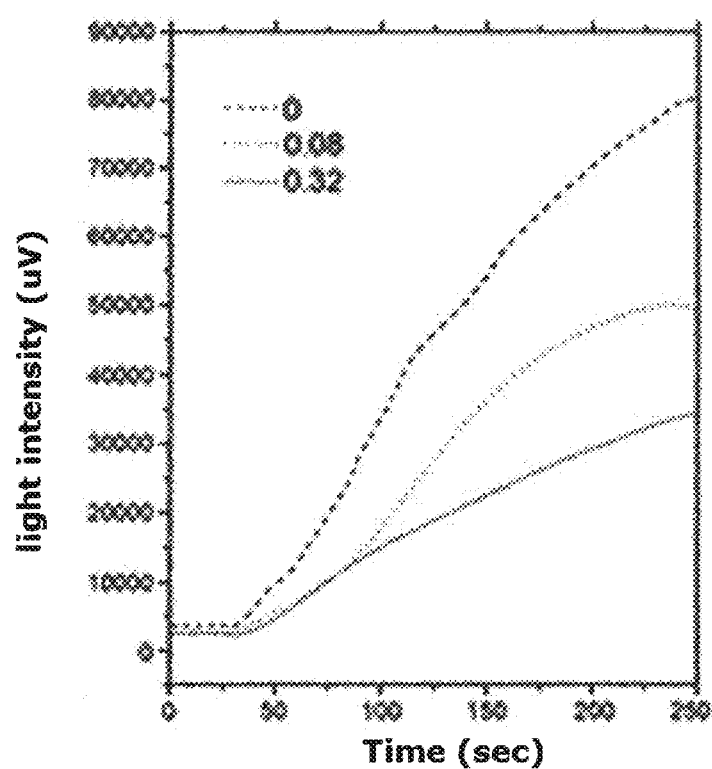

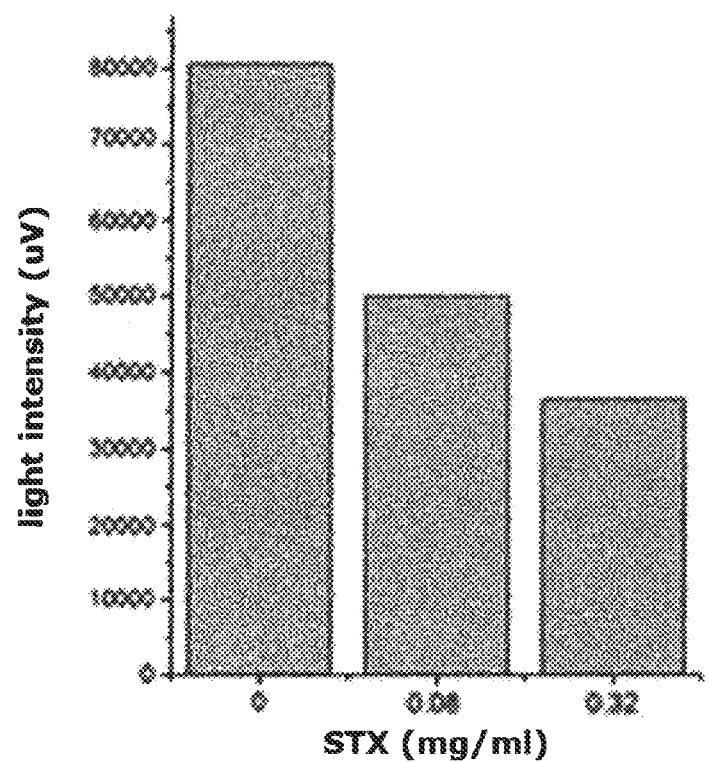
[FIG. 28B]

[FIG. 29]
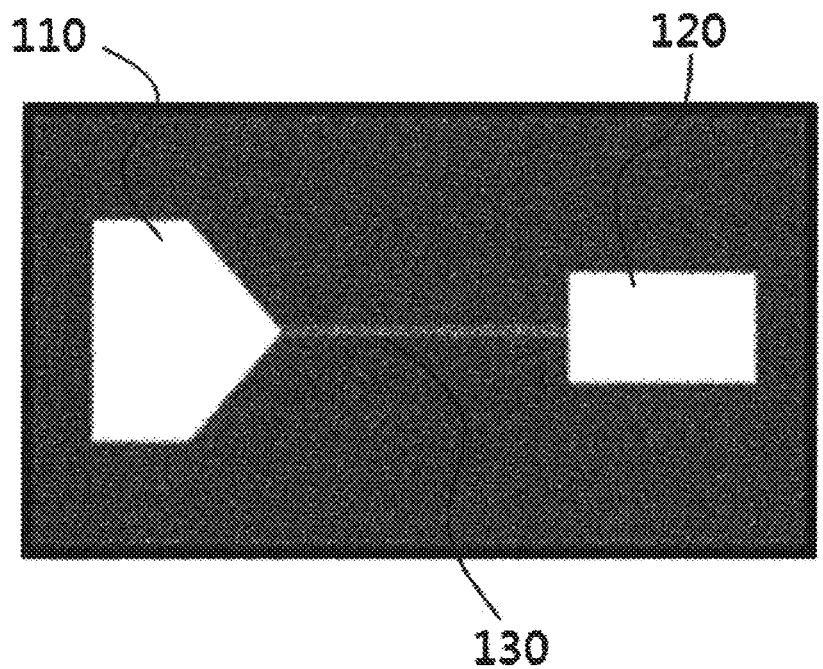
[FIG. 30]
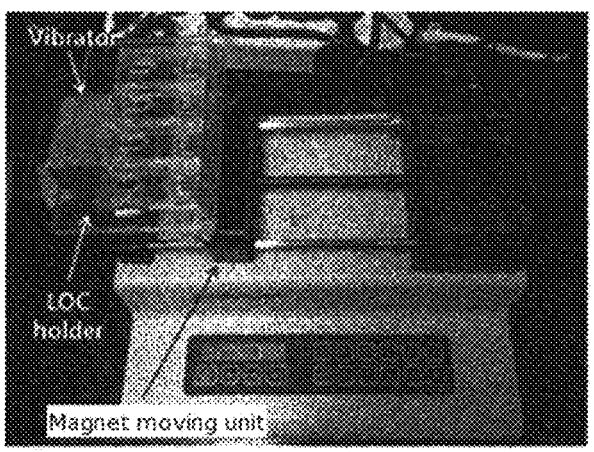
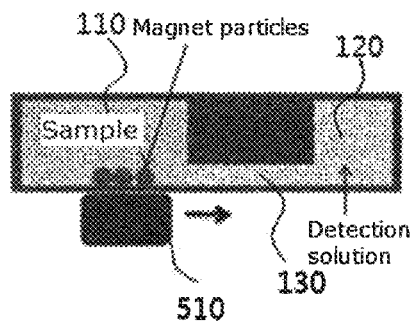

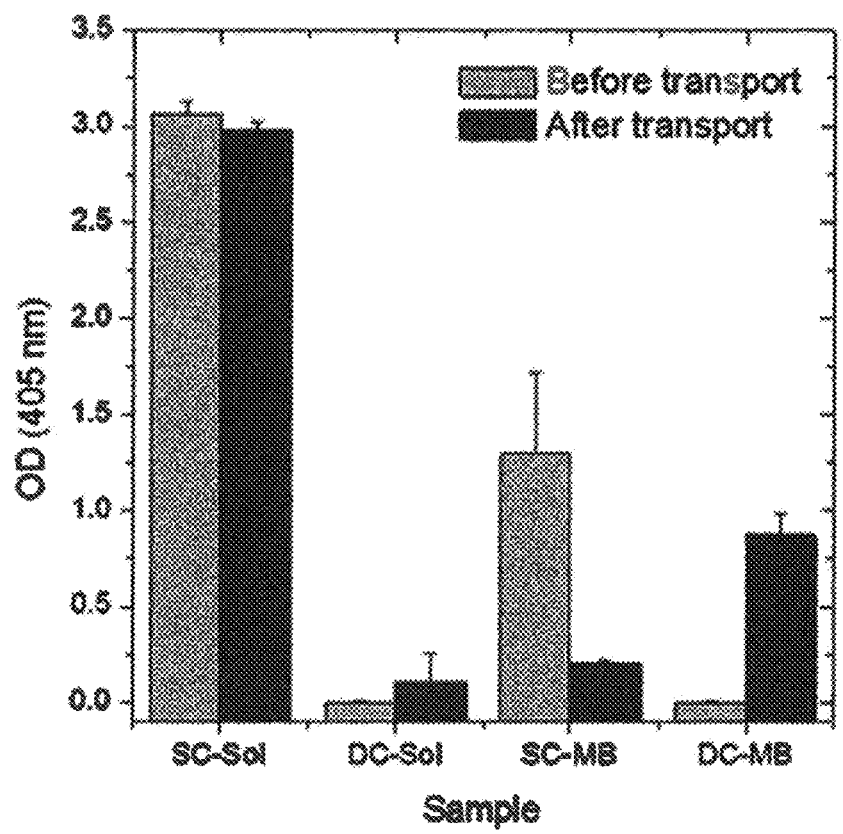
[FIG. 31]

[FIG. 32]
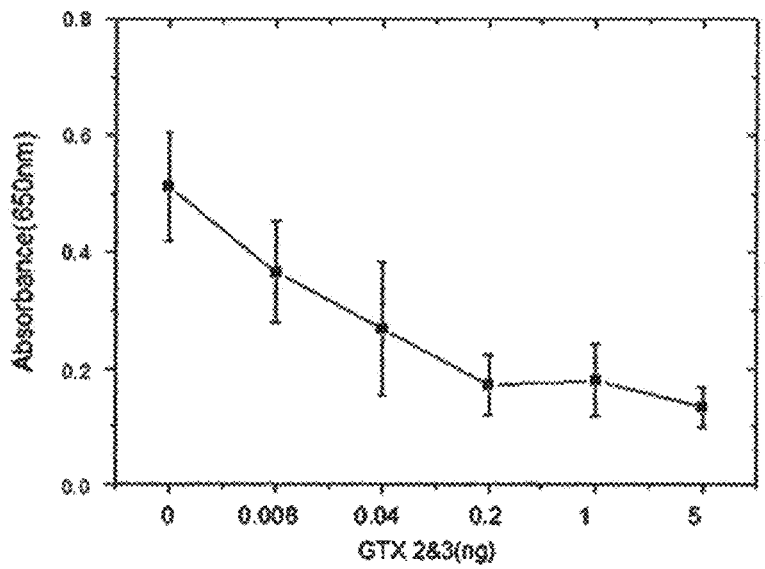
[FIG. 33]
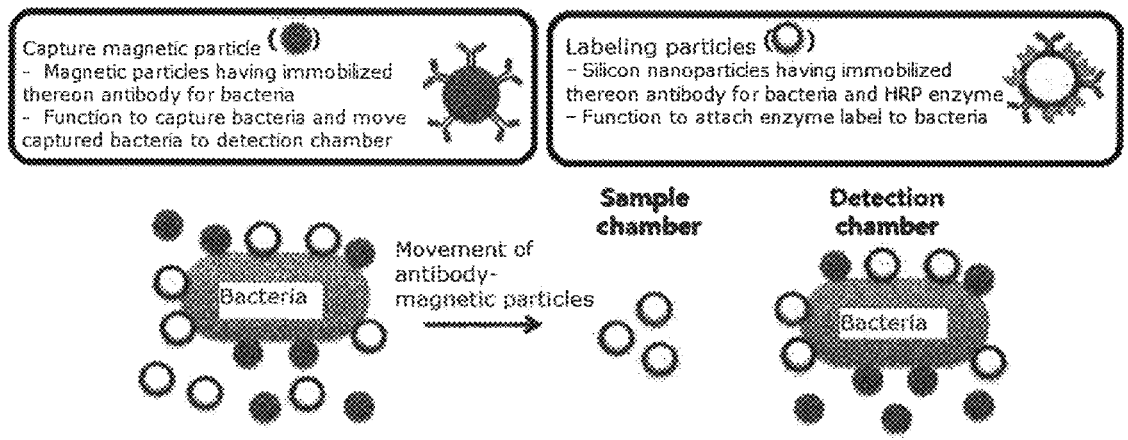

[FIG. 34]
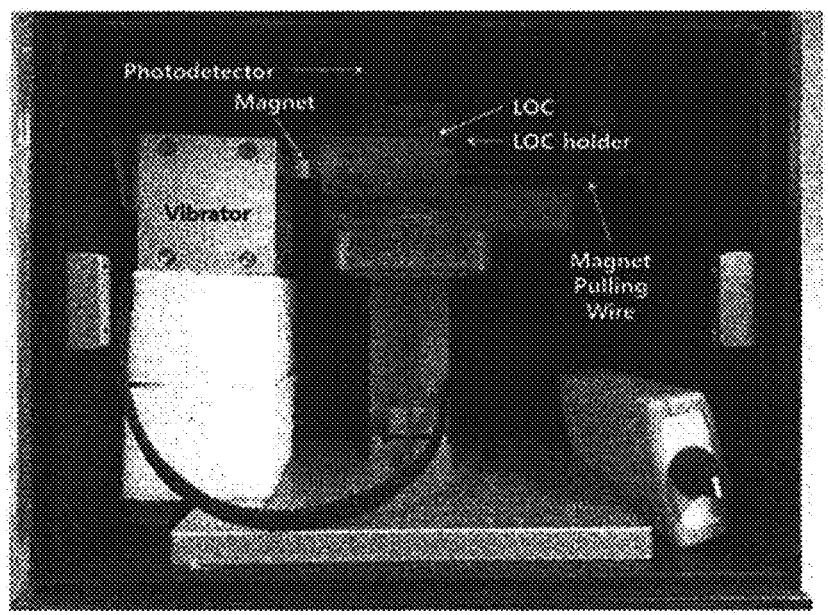
[FIG. 35]
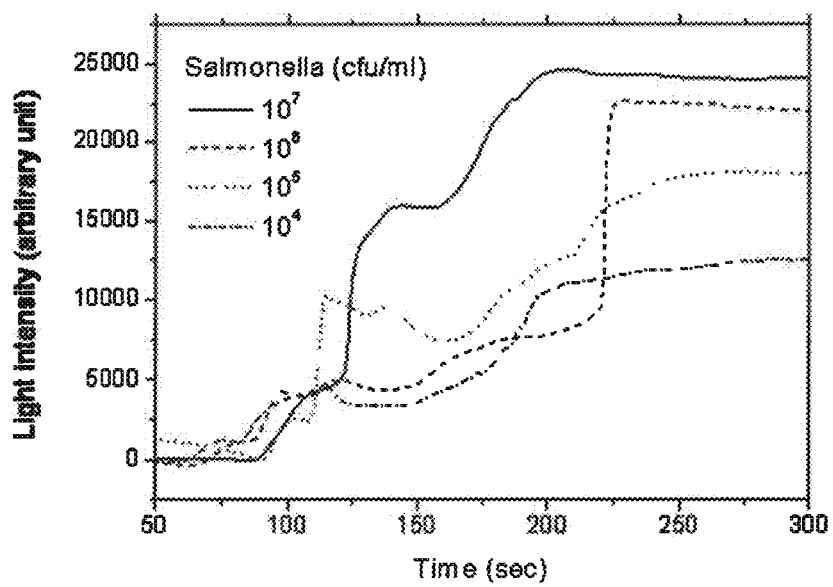

METHODS FOR DETECTING AN ANALYTE USING AN ANALYTE DETECTION DEVICE

CROSS REFERENCE TO RELATED APPLICATION

This application resulted from a division of U.S. patent application Ser. No. 14/915,206, which was filed Feb. 26, 2016, which claims priority to and is a 371 of International Application No. PCT/KR2014/007976, which was filed on Aug. 27, 2014, and which claims priority to Korean Patent Application No. 10-2013-0102944, which was filed on Aug. 29, 2013, and Korean Patent Application No. 10-2013-0166909, which was filed on Dec. 30, 2013, and the teachings of all the applications are incorporated herein by reference.

TECHNICAL FIELD

The present invention relates to a device and method for detecting an analyte by movement of particles.

BACKGROUND ART

Immunoassays such as ELISA (enzyme-linked immunosorbent assay) are antibody-based detection methods and are widely used in disease diagnosis or research. For example, a sandwich ELISA method uses two kinds of antibodies that bind to different sites of an analyte. Of the two antibodies, one antibody is immobilized on a solid phase such as an immunoplate and used as a capture antibody, and the other antibody is linked to an enzyme and used as a labeled antibody. When a sample containing an analyte is added to and reacted with the solid phase having the capture antibody immobilized thereon, the analyte binds to the antibody. In this state, when the surface of the solid phase is washed with a washing butter, all substances other than the analyte can be removed from the surface. When the labeled antibody is then added to and reacted with the solid phase and unbound labeled antibody is washed out with a washing buffer, the enzyme binds to the solid phase in proportion to the amount of the analyte. Thus, the amount of the analyte can be measured by measuring the activity of the enzyme.

Herein, the reason why the antibody is immobilized on the solid phase is because substances remaining in the liquid phase without binding to the solid phase can be easily removed. In other immunoassays, a secondary antibody or protein G capable of binding to the antibody may be immobilized on the solid phase, or an antigen may also be immobilized on the solid phase.

As the solid phase, a plastic surface such as an immunoplate is frequently used, but particles may also be used due to its advantages such as a large surface area. Particularly, magnetic particles have an advantage in that they can be captured or moved using a magnet, and thus are frequently used in a pretreatment process for setting an analyte from a sample containing a large amount of impurities. For example, when magnetic particles having immobilized thereon an antibody for an analyte are added to and reacted with a sample, the analyte binds to the antibody immobilized on the magnetic particles. When a magnetic force is applied to the wall of a tube containing the sample, the magnetic particles all adhere to the tube wall, and impurities can ail be removed by removing the remaining solution.

However, because liquid should be transferred in order to automate conventional immunoassays, a pump is required. Further, a container for storing a washing buffer and tubes for transferring liquid are required in an immunoassay device. In addition, a transfer unit for moving an immunoplate or a liquid injection unit is required. For these reasons, there is a disadvantage in that the device is large and complex.

DISCLOSURE

Technical Problem

The present invention is intended to provide an analyte detection device and method, which can easily detect an analyte by moving the analyte from a sample chamber to a detection chamber.

Technical Solution

The present invention provides an analyte detection device comprising: a sample chamber configured to contain a mixed solution of a reactant comprising particles and a sample an analyte; a detection chamber configured to contain a detection solution; and a channel located between the sample chamber and the detection chamber so as to prevent the mixed solution and the detection solution from mixing with each other, wherein the analyte is detected by moving the particles from the sample chamber to the detection chamber using moving means.

The present invention also provides a method for detecting an analyte using an analyte detection device, the analyte detection device comprising: a sample chamber configured to contain a mixed solution of a reactant comprising particles and a sample containing the analyte; a detection chamber configured to contain a detection solution; and a channel located between the sample chamber and the detection chamber so as to prevent the mixed solution and the detection solution from mixing with each other; the method comprising the steps of: mixing and reacting the sample containing the analyte with the reactant comprising the particles in the sample chamber; moving the particles to the detection chamber by moving means; and detecting the analyte in the detection chamber.

The present invention also provides a method for detecting an analyte using an analyte detection device, the analyte detection device comprising: a sample chamber configured to contain a mixed solution of a reactant comprising capture particles and labeling particles and a sample containing the analyte; a detection chamber configured to contain a detection solution; and a channel located between the sample chamber and the deletion chamber so as to prevent the mixed solution and the detection solution from mixing with each other; the method comprising the steps of: mixing the reactant with the sample in the sample chamber to form a capture particle-analyte-labeling particle complex; moving the capture particle-analyte-labeling particle complex to the detection chamber by moving means; and detecting the analyte in the detection chamber.

The present invention also provides a method for detecting an analyte using an analyte detection device, the analyte detection device comprising: a sample chamber configured to contain a mixed solution of a sample containing the analyte and a reactant comprising capture particles having immobilized thereon a primary receptor specific for the analyte and a labeled standard material having a label linked to a standard material; a detection chamber configured to contain a detection solution; and a channel located between the sample chamber and the detection chamber so as to prevent the mixed solution and the detection solution from mixing with each other; the method comprising the steps of: mixing the reactant and the sample in the sample chamber to form a capture particle-analyte complex and a capture particle-labeled standard material complex; moving the capture particle-analyte complex and the capture particle-labeled standard material complex to the detection chamber by moving means; and detecting the analyte in the detection chamber by use of the label linked to the labeled standard material, wherein the standard material is capable of binding to the primary receptor competitively with the analyte.

The present invention also provides a method for detecting an analyte using an analyte detection device, the analyte detection device comprising: a sample chamber configured to contain a mixed solution of a sample containing the analyte and a reactant which comprises capture particles having immobilized thereon a primary receptor specific for the analyte and a secondary receptor specific for the primary receptor and which also comprises a labeled standard material having a label linked to a standard material; a detection chamber configured to contain a detection solution; and a channel located between the sample chamber and the detection of chamber so as to prevent the mixed solution and the detection solution from mixing with each other; the method comprising the steps of: mixing the reactant and the sample in the sample chamber to form a capture particle-primary receptor-analyte complex and a capture particle-primary receptor-labeled standard material complex; moving the capture particle-primary receptor-analyte complex and the capture particle-primary receptor-labeled standard material complex to the detection chamber by moving means; and detecting the analyte in the detection chamber by use of the label linked to the standard material, wherein the standard material is capable of binding to the primary receptor competitively with the analyte.

The present invention also provides a method for detecting an analyte using an analyte detection device, the analyte detection device comprising: a sample chamber configured to contain a mixed solution of a sample containing an analyte and a reactant comprising capture particles having immobilized thereon a first receptor specific for the analyte and a labeled receptor having a label attached to a second receptor specific for the analyte; a detection chamber configured to contain a detection solution; and a channel located between the sample chamber and the detection chamber so as to prevent the mixed solution and the detection solution from mixing with each other; the method comprising the steps of: mixing the reactant and the sample in the sample chamber to form a capture particle-analyte-labeled receptor complex; moving the capture particle-analyte-labeled receptor complex to the detection chamber by moving means; and detecting the analyte using the label attached to the labeled receptor, wherein the first receptor and the second receptor are capable of binding non-competitively to different sites of the analyte.

The present invention also provides a system for detecting an analyte using gravity, comprising: an analyte detection device comprising a sample chamber configured to contain a mixed solution of a reactant comprising particles and a sample containing an analyte, a detection chamber formed below the sample chamber and configured to contain a detection solution, and a channel located between the sample chamber and the detection chamber so as to prevent the mixed solution and the detection solution from mixing with each other; and at least one valve between the sample chamber and the channel, wherein the particles have a specific gravity greater than that of the mixed solution and the detection solution of the sample.

The present invention also provides a method for detecting an analyte using gravity, which uses the system for detecting the analyte using gravity and comprises the steps of: reacting the reactant with the sample in the sample chamber in a state in which the valve is closed; opening the valve to move the particles to the detection chamber; and detecting the analyte in the detection chamber.

The present invention also provides a system for detecting an analyte using gravity, the system comprising an analyte detection device comprising: a sample chamber configured to contain a mixed solution of a reactant comprising particles and a sample containing the analyte; a detection chamber configured to contain a detection solution; and a channel located between the sample chamber and the detection chamber so as to prevent the mixed solution and the detection solution from mixing with each other, wherein the channel is configured to connect the upper portion of the sample chamber with the upper portion of the detection chamber in a state in which the sample chamber and the detection chamber are horizontally positioned, and the particles have a specific gravity greater than that of each of the mixed solution and the detection solution of the sample.

The present invention also provides a method for detecting an analyte rising gravity, which uses the system for detecting the analyte using gravity and comprises the steps of: reacting the reactant with the sample in the sample chamber; inclining the analyte detection device at an angle of 20-70° such that the channel faces downward, thereby moving the particles to the detection chamber; and detecting the analyte in the detection chamber.

The present invention also provides a system for detecting an analyte using a centrifugal force, comprising: an analyte detection device comprising a sample chamber configured to contain a mixed solution of a reactant comprising particles and a sample containing the analyte, a detection chamber configured to contain a detection solution, and a channel located between the sample chamber and the detection chamber so as to prevent the mixed solution and the detection solution from mixing with each other; a disc which includes a plurality of the analyte detection devices and is rotatable; and at least one detector located near the disc, wherein the sample chamber is disposed toward the center of the disc, and the detection chamber is disposed outward from the center of the disc.

The present invention also provides a method for detecting an analyte using a centrifugal force, which uses the system for detecting the analyte using the centrifugal force and comprises the steps of: reacting the reactant with the sample in the sample chamber; rotating the disc to open the valve and the channel; moving the particles to the detection chamber; and stopping the rotation, and then rotating the disc at an angle of 10-180° such that the detection chambers of the detection devices sequentially face toward the detector, and detecting the analyte in each of the detection chambers.

The present invention also provides a system for detecting an analyte using a magnetic force, the system comprising: an analyte detection device comprising a sample chamber configured to contain a mixed solution of a sample containing the analyte and a reactant comprising labeling capture particles which comprises a label attached to magnetic particles and have immobilized thereon a receptor for the analyte, a detection chamber configured to contain a detection solution, and a channel located between the sample chamber and the detection chamber so as to prevent the mixed solution and the detection solution from mixing each other; a filter disposed on the bottom inside the analyte detection device; and at least one magnetic force application unit disposed on the outer wall of the bottom of the analyte detection device and configured to apply a magnetic force to the labeling capture particles, wherein the channel is configured to connect the bottom of the simple chamber with the bottom of the detection chamber in a state in which the sample chamber and the detection chamber are horizontally disposed.

The present invention also provides a method for detecting an analyte using a magnetic force, which uses the system for detecting the analyte using the magnetic force and comprises the steps of: reacting the reactant with the sample in the sample chamber; applying a magnetic force from the detection chamber to the sample chamber using the magnetic force application unit disposed on one side of the detection chamber, thereby moving the magnetic particles from the sample chamber to the detection chamber, and detecting the analyte in the detection chamber.

The present invention also provides a method for detecting an analyte using a magnetic force, which uses the system for detecting the analyte using the magnetic force and comprises the steps of: reacting the reactant with the sample in the sample chamber; moving the magnetic force application unit from the sample chamber to the detection chamber in a state in which the magnetic force application unit is located on the outside of the analyte detection device, thereby moving the magnetic particles from the sample chamber to the detection chamber; and detecting the analyte in the detection chamber.

The present invention also provides a system for detecting an analyte using a magnetic force, the system comprising: an analyte detection device comprising a sample chamber configured to contain a mixed solution of a sample containing the analyte and a reactant comprising labeling capture magnetic particles which have a label attached thereto and have immobilized thereon a receptor for the analyte, a detection chamber configured to contain a detection solution, and a channel located between the sample chamber and the detection chamber so as to prevent the mixed solution and the detection solution from mixing with each other; a filter disposed on the bottom inside the analyte detection device; and at least one magnetic force application unit disposed on the outer wall of the bottom of the analyte detection device and configured to apply a magnetic force to the labeling capture magnetic particles, wherein the channel is configured to connect the bottom of the sample chamber with the bottom of the detection chamber in a state in which the sample chamber and the detection chamber are horizontally disposal.

The present invention also provides a method for detecting an analyte using a magnetic force, which uses the system for detecting the analyte using the magnetic force and comprises the steps of: reacting the reactant with the sample in the sample chamber to form a labeling capture particle-analyte complex; moving the magnetic force application unit from the sample chamber to the detection chamber, thereby discharging labeling capture particles unbound to the analyte to the bottom of the filter and moving the labeling capture particle-analyte complex to the detection chamber, and detecting the analyte in the detection chamber by use of the label attached to the labeling capture particles.

The present invention also provides a system for detecting an analyte using a magnetic force and a centrifugal force, the system comprising: an analyte detection device comprising a sample chamber configured to contain a mixed solution of a sample containing the analyte and a reactant comprising labeling capture particles which comprise a label attached to magnetic particles and have immobilized thereon a receptor for the analyte, a detection chamber configured to contain a detection solution, and a channel located between the sample chamber and the detection chamber so as to prevent the mixed solution and the detection solution from mixing with each other; a filter disposed on the bottom inside the analyte detection device; at least one magnetic force application unit disposed on the outer wall of the bottom of the analyte detection device and configured to apply a magnetic force to the labeling capture particles; a disc which includes a plurality of the analyte detection devices and is rotatable; and at least one detector located near the disc, wherein the sample chamber is disposed toward the center of the disc, the detection chamber is disposed outward from the center of the disc, and the channel is configured to connect the bottom of the sample chamber with the bottom of the detection chamber.

The present invention also provides a method for detecting an analyte using a magnetic force and a centrifugal force, which uses the system for detecting the analyte using the magnetic force and the magnetic force and comprises the steps of: reacting the reactant with the sample in the sample chamber to form a labeling capture particle-analyte complex; rotating the disc in a state in which the magnetic force application unit is fixed to the bottom of the sample chamber, thereby discharging labeling capture particles unbound to the analyte to the bottom of the filter and moving the labeling capture particle-analyte complex to the detection chamber; and detecting the analyte in the detection chamber by use of the label attached to the labeling capture particles.

Advantageous Effects

The analyte detection device according to the present invention does not require units for moving solutions, and thus is highly economical.

DESCRIPTION OF DRAWINGS

FIG. 1 illustrates an analyte detection device according to the present invention.

FIG. 2 illustrates that a labeling chamber is additionally provided between a sample chamber and a detection chamber according to the present invention.

FIG. 3 illustrates that a waste chamber is additionally provided in a detection chamber according to the present invention.

FIG. 4 illustrates that a reactant chamber connected to a sample chamber according to the present invention is additionally disposed.

FIG. 5 illustrates a method in which a reactant is injected by moving a reactant chamber plug using a fixing cover having a protrusion formed thereon according to the present invention.

FIG. 6 illustrates a method in which a dried reactant is dissolved using a solvent stored in a reactant chamber and is injected into a sample chamber according to the present invention.

FIG. 7 illustrates a method in which a washing buffer is injected by moving a washing buffer chamber plug using a fixing cover having a protrusion formed thereon according to the present invention.

FIG. 8 illustrates a system for detecting an analyte using gravity according to the present invention.

FIG. 9 illustrates a system for detecting an analyte using gravity according to the present invention.

FIG. 10 illustrates a system for detecting an analyte using a centrifugal force according to the present invention.

FIG. 11 illustrates a system for detecting an analyte using a centrifugal force according to the present invention.

FIG. 12 illustrates a valve that is opened or closed by a centrifugal force using a cam having a weight connected thereto in a system for detecting an analyte using a centrifugal force according to the present invention.

FIG. 13 illustrates a valve that is opened or closed by a centrifugal force using a horizontally movable clamp in a system for detecting an analyte using a centrifugal force according to the present invention.

FIG. 14 illustrates a method in which magnetic particles are moved from a sample chamber to a sample direction by applying a magnetic force in a direction from the detection chamber to the sample chamber in a system for detecting an analyte using a magnetic force according to the present invention.

FIG. 15 illustrates a method in which magnetic particles are moved by moving a magnet.

FIG. 16 illustrates a method in which different kinds of particles are separated from each other using a magnetic force together with a centrifugal force according to the present invention.

FIG. 17 illustrate a method in which bacteria are detected using capture particles (capture magnetic particles) having immobilized thereon a receptor for the bacteria and labeling particles (labeling receptor particles) which have immobilized thereon a receptor for the bacteria, and have a labeling function, according to the present invention.

FIG. 18 illustrates a method in which magnetic particles unbound to bacteria are removed by disposing a filter on an inner surface opposite an outer surface with which a magnet comes into contact, and moving the magnet, according to the present invention.

FIG. 19 illustrates a method in which magnetic particles unbound to bacteria are removed by using a centrifugal force together with a force in a state in which a filter is disposed on an inner surface opposite an outer surface with which a magnet comes into contact, according to the present invention.

FIG. 20 illustrates a method in which an analyte is detected by a sandwich ELISA method using capture particles having a capture antibody immobilized thereon and a labeled antibody according to the present invention.

FIG. 21 illustrates a method in which the analyte kinase is detected by immobilizing on particles a receptor for a material produced by the analyte according to the present invention.

FIG. 22 illustrates a method in which the analyte protease is detected by immobilizing on particles a receptor for a material dissociated by the analyte according to the present invention.

FIG. 23 illustrates a principle according to which paralytic shellfish toxin (STX) is detected by a competitive immunoassay using magnetic particles as a solid phase in a detection device according to the present invention.

FIG. 24 shows the structure of a detection device used in Example 1.

Figure 25:
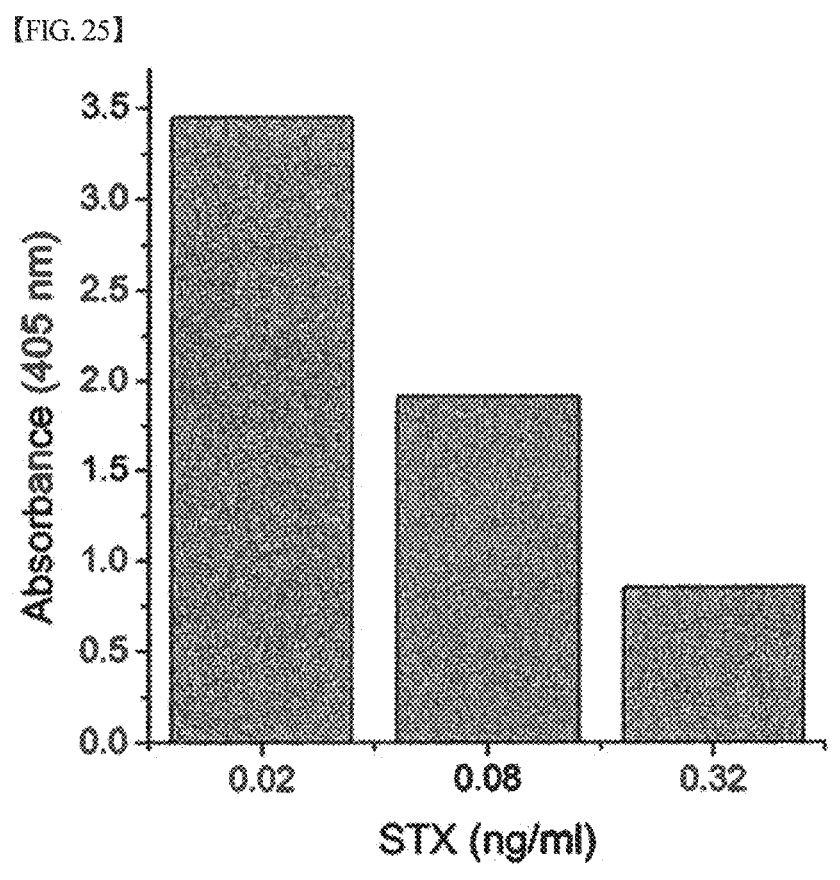

FIG. 25 is a graph showing the results of detecting paralytic shellfish toxin (STX) by a competitive immunoassay in Example 1.

FIG. 26 shows the LOC structure of a detection device used in Example 2.

FIGS. 27A and 27B show the structure and operating principle of a measurement device used in Example 2.

FIGS. 28A and 28B are a graph showing the results of detecting the paralytic shellfish toxin STX by a competitive immunoassay in Example 2.

FIG. 29 shows the LOC structure of a detection device used in Example 3.

FIG. 30 shows the structure and operating principle of a magnetic particle moving device used in Example 3.

FIG. 31 is a graph showing the results of an experiment performed in Example 3 to confirm whether or not solutions of the sample chamber and detection chamber of an LOC are mixed with each other and whether or not other materials of the sample chamber also move during movement of particles of the sample chamber.

FIG. 32 is a graph showing the results of detecting paralytic shellfish toxin GTX 2&3 by a competitive immunoassay in Example 3.

FIG. 33 shows a principle according to bacteria are detected using capture particles (capture magnetic particles) and labeling particles (labeling particles) in Example 4.

FIG. 34 is a photograph showing a measurement device used in Example 4.

FIG. 35 is a graph showing the results of detecting *Salmonella* bacteria in Example 4.

BEST MODE

Hereinafter, preferred embodiments of the present invention will be described in detail with reference to the accompanying drawings.

The terms and words used in the specification and claims should not be interpreted as being limited to typical meanings or dictionary definitions, but should be interpreted as having meanings and concepts relevant to the technical scope of the present invention, based on the principle according to which the inventors can appropriately define the concept of the terms to describe their invention in the best manner.

Therefore, the configurations described in the embodiments and drawings of the present invention are merely the most preferable embodiments, but do not represent all of the technical spirit of the present invention. Thus, it should be understood that various equivalents and modifications that replace these embodiments are possible at the time of filing of this application.

FIG. 1 illustrates an analyte detection device according to the present invention; FIG. 2 illustrates that a labeling chamber is additionally provided between a sample chamber and a detection chamber according to the present invention; FIG. 3 illustrates that a waste chamber is additionally provided in a detection chamber according to the present invention; FIG. 4 illustrates that a reactant chamber connected to a sample chamber according to the present invention is additionally disposed; FIG. 5 illustrates a method in which a reactant is injected by moving a reactant chamber plug using a fixing cover having a protrusion formed thereon according to the present invention; FIG. 6 illustrates a method in which a dried reactant is dissolved using a solvent stored in a reactant chamber and is injected into a sample chamber according to the present invention; FIG. 7 illustrates a method in which a washing buffer is injected by moving a washing buffer chamber plug using a fixing cover having a protrusion formed thereon according to the present invention; FIG. 8 illustrates a system for detecting an analyte using gravity according to the present invention; FIG. 9 illustrates a system for detecting an analyte using gravity according to the present invention; FIG. 10 illustrates a system for detecting an analyte using a centrifugal force according to the present invention; FIG. 11 illustrates a system for detecting an analyte using a centrifugal force according to the present invention; FIG. 12 illustrates a valve that is opened or closed by a centrifugal force using a cam having a weight connected thereto in a system for detecting an analyte using a centrifugal force according to the present invention; FIG. 13 illustrates a valve that is opened or closed by a centrifugal force using a horizontally movable clamp in a system for detecting an analyte using a centrifugal force according to the present invention; FIG. 14 illustrates a method in which magnetic particles are moved from a sample chamber to a sample direction by applying a magnetic force in a direction from the detection chamber to the sample chamber in a system for detecting an analyte using a magnetic force according to the present invention; FIG. 15 illustrates a method in which magnetic particles are moved by moving a magnet; FIG. 16 illustrates a method in which different kinds of particles are separated from each other using a magnetic force together with a centrifugal force according to the present invention; FIG. 17 illustrates a method in which bacteria are detected using capture particles (capture magnetic particles) having immobilized thereon a receptor for the bacteria and labeling particles (labeling receptor particles) which have immobilized thereon a receptor for the bacteria and have a labeling function, according to the present invention; FIG. 18 illustrates a method in which magnetic particles unbound to bacteria are removed by disposing a filter on an inner surface opposite an outer surface with which a magnet comes into contact and moving the magnet, according to the present invention; FIG. 19 illustrates a method in which magnetic particles unbound to bacteria are removed by using a centrifugal force together with a magnetic force in a state in which a filter is disposed on an inner surface opposite an outer surface with which a magnet comes into contact, according to the present invention; FIG. 20 illustrates a method in which an analyte is detected by a sandwich ELISA method using capture particles having a capture antibody immobilized thereon and a labeled antibody according to the present invention; FIG. 21 illustrates a method in which the analyte kinase is detected by immobilizing on particles a receptor for a material produced by the analyte according to the present invention; FIG. 22 illustrates a method in which the analyte protease is detected by immobilizing on particles a receptor for a material dissociated by the analyte according to the present invention; FIG. 23 illustrates a principle according to which paralytic shellfish toxin (STX) is dieted by a competitive immunoassay using magnetic particles as a solid phase in a detection device according to the present invention; FIG. 24 shows the structure of a detection device used in Example 1; FIG. 25 is a graph showing the results of detecting paralytic shellfish toxin (STX) by a competitive immunoassay in Example 1; FIG. 26 shows the LOC structure of a detection device used in Example 2; FIG. 27 shows the structure and operating principle of a measurement device used in Example 2; FIG. 28 is a graph showing the results of detecting the paralytic shellfish toxin STX by a competitive immunoassay in Example 2; FIG. 29 shows the LOC structure of a detection device used in Example 3; FIG. 30 shows the structure and operating principle of a magnetic particle moving device used in Example 3; FIG. 31 is a graph showing the results of an experiment performed in Example 3 to confirm whether or not solutions of the sample chamber and detection chamber of an LOC are mixed with each other and whether or not other materials of the sample chamber also move during movement of particles of the sample chamber; FIG. 32 is a graph showing the results of detecting paralytic shellfish toxin GTX 2&3 by a competitive immunoassay in Example 3; FIG. 33 shows a principle according to bacteria are detected using capture particles (capture magnetic particles) and labeling particles (labeling particles) in Example 4; FIG. 34 is a photograph showing a measurement device used in Example 4; FIG. 35 is a graph showing the results of detecting *Salmonella* bacteria in Example 4. Hereinafter, an analyte detection device, an analyte detection system and an analyte detection method according to the present invention will be described in described with reference to FIGS. 1 to 35 and examples.

As shown in FIG. 1, an analyte detection device 100 according to the present invention comprises a sample chamber 110 and a detection chamber 120, and may comprise a channel 130 between the sample chamber 110 and the detection chamber 120. More specifically, the sample chamber 110 may receive a mixed solution of a reactant comprising particles 200 and a sample containing an analyte 210, and the detection chamber 120 may receive a detection solution. In addition, the diameter of the channel 130 may be smaller than the diameter of each of the sample chamber 110 and the detection chamber 120 in order to prevent the mixed solution and the detection from mixing with each other.

In the present invention, the particles 200 may be a material that is bound to the analyte 210 or a product produced by the analyte 210 to form a particle-analyte complex or a particle-product complex. For this, either a receptor specific for the analyte 210 or a receptor specific for a product produced by the analyte 210 may be immobilized on the particles 200. Particularly, the particles 200 may function to move the analyte 210 or a product produced by the analyte 210 from the sample chamber 110 to the detection chamber 120, and may also function to attach a label to the analyte 210.

In addition, the particles 200 may be at least one kind of particles selected from the group consisting of silica particles, polystyrene particles, polycarbonate particles, glass particles, alumina particles, gold particles, silver particles, palladium particles, platinum particles, titania particles, zirconium particles, and core-shell particles.

In the present invention, the receptor immobilized on the particles may be a receptor capable of binding directly to the analyte 210. More specifically, if the analyte 210 is one of substances such as proteins, organic molecules, viruses, bacteria, plant cells or animal cells, for which antibodies can be formed, an antibody for each analyte 210 may be used as the receptor. As an example, if the analyte 210 is lectin, a carbohydrate may be used as the receptor, and on the contrary, if the analyte 210 comprises a carbohydrate, lectin may be used as the receptor. As another example, if the analyte 210 is nucleic acid such as DNA or RNA, a DNA or PNA (peptide nucleic acid) having a nucleotide sequence complementary thereto may be used as the receptor. In addition, any substances, including aptamers obtained from nucleic acids, peptide ligands obtained from peptide libraries, protein ligands obtained from affibody libraries, etc., may be used as the receptor, as long as the analyte 210 may bind specifically thereto.

In a specific embodiment, a receptor capable of binding a receptor that binds directly to the analyte may be immobilized on the particles. In this case, in order to distinguish between the two different receptors, the receptor that binds directly to the analyte is referred herein to as the primary receptor, and the receptor that binds to the primary receptor is referred herein to as the secondary receptor. More specifically, if the primary receptor is an antibody, the secondary receptor used may be a secondary antibody or protein G. As another example, if the primary receptor is DNA or PNA (peptide nucleic acid), a DNA or PNA complementary to a portion of the nucleotide sequence of the primary receptor may be used as the secondary receptor.

Herein, the secondary antibody used may be, for example, an anti-rabbit immunoglobulin G antibody, if the primary antibody is of rabbit origin.

In another specific embodiment, the receptor may be a receptor capable of binding to a substance produced by the analyte 210, and the analyte 210 may be an enzyme. More specifically, the receptor may be a receptor for a substance that is produced in proportion to the amount of the analyte 210. For example, if the analyte 210 is an enzyme, the receptor may be a receptor for the product. As another example, a receptor for a molecule that is dissociated or structurally changed in response to the analyte 210 may also be used.

Particularly, the present invention is characterized in that the mixed solution and the detection solution are received in a stationary state, and the detection chamber 210 may be closed other than the portion collected to the channel 130.

As used herein, the expression "the mixed solution and the detection solution are stationary" does not mean that the solutions do not move, but means that analysis can be performed by moving the solid phase instead of moving the liquid phase in a main analysis step, unlike a conventional method in which the liquid phase is moved. As used herein, the term "solid phase" may refer to particles.

Furthermore, the detection solution may be filled in the channel 130. In addition, in order to more effectively remove impurities when the particles 200 pass through the channel 130, a washing buffer may be filled in the channel 130.

As used herein, the term "washing buffer" refers to a buffer containing components that assist in removing non-specifically adsorbed substances from the particles, such as an appropriate concentration of detergent or salt.

As shown in FIG. 2, the analyte detection device 100 according to the present invention may further comprise a labeling chamber 140 containing a labeling solution. The labeling chamber 140 may be connected between the sample chamber 110 and the detection chamber 120 by the channel 130, and the labeling solution 230 may comprise a labeled receptor 230.

Herein, the labeled receptor 230 means one having a label attached to a receptor capable of binding to the analyte 210, and the label may be at least one selected from the group consisting of color development, luminescence, fluorescence, catalytic activity, magnetic force, and radioactivity.

More specifically, the labeling chamber 140 may be used in a sandwich method in which capture particles having immobilized thereon a receptor capable of binding to the analyte 210 are added to a sample obtaining the analyte 210 to bind the analyte 210 to the capture particles which are then washed, after which the labeled receptor 230 is added thereto to bind the analyte 210. Herein, the reason why the particles used are referred to as the capture particles 220 is because these particles serve to capture and move the analyte. Herein, the receptor immobilized on the capture particles 220 and the used in the labeled receptor should be able to simultaneously bind non-competitive to different sites of the analyte. In addition, the two receptors are referred herein to as the first receptor and the second receptor, respectively, in order to distinguish from the above-described primary receptor and secondary receptor.

Particularly, as an example, when a sample containing the analyte 210 and the capture particles 220 are added to the sample chamber 110 and reacted with each other, the analyte 210 can be bound to the capture particles 220. When the capture particles 220 are moved to the labeling chamber 140, substances unbound to the capture particles 220 can be washed out during passage through the channel 130, and the labeled receptor 230 can bind to the analyte 210 in the labeling chamber 140, and thus a sandwich form can be detained. Finally, when the capture particles 220 are moved to the detection chamber 120, substances unbound to the particles can be washed out during passage through the channel 130, and the amount of the analyte 210 can be evaluated by measuring the signal of the label bound to the capture particles in the detection chamber.

In another simple method that performs a sandwich method according to the present invention, a sample, the capture particles 220 and the labeled receptor 230 may be added to the detection device of FIG. 1 and reacted with one another, and then the capture particles 200 may be moved to the detection chamber 120, thereby detecting the analyte.

As shown in FIG. 3, the detection chamber 120 according to the present invention may contain, on at least one side, a receptor to which the particles 200 can bind, and the analyte detection device of the present invention may further comprise a waste chamber 150 configured to receive particles 200 unbound to the receptor 200. The waste chamber 150 may be connected to one side of the detection chamber 120.

In particular, the detection device shown in FIG. 3 may be used to detect the analyte 210 by a sandwich method using the labeling capture particles 220 which have immobilized thereon a receptor and function as a label. Among the two kinds of receptors that are used in the sandwich method, the first receptor may be placed in the detection chamber 120 as described above, and the second receptor may be immobilized on the particles 200. Of course, in this case, the two receptors should be receptors that bind to different sites of the analyte so as not to overlap each other.

For example, if an enzyme is used as a label, the enzyme together with the first receptor may be bound to the particles 200. In addition, if fluorescence is used as a label, the receptor may be immobilized on particles 200 capable of emitting fluorescence. When a sample containing the analyte 210 and the labeling capture particles 240 are added to the sample chamber 110 and reacted with each other, the analyte 210 may bind to the labeling capture particles 240, and when the labeling capture particles 240 are moved to the detection chamber 120, the labeling capture particles 240 bound to the analyte 210 can bind to the second receptor via the analyte 210. Unbound labeling capture particles 240 continue to move from the detection chamber to the waste chamber 150. Thus, the amount of the analyte 210 can be evaluated by measuring the signal of the label in the detection chamber 120 and the waste chamber 150.

As shown in FIGS. 4 to 7, the analyte detection device according to the present invention may further comprise a reactant chamber 160 connected to one side of the sample chamber 110 and containing a reactant 113.

More specifically, the reactant chamber 160 may be connected to one side of the sample chamber 110 through a first connection passage 131, and the diameter of the first connection passage 131 may be smaller than that of each of the reaction chamber 160 and the sample chamber 110. In addition, the reaction chamber 160 comprises a first cavity formed therein, and a reactant chamber plug 112 disposed in the upper portion of the first cavity so as to be movable up and down by external pressure, wherein the reactant 113 is placed in the lower portion of the first cavity so that it will be discharged to the first connection passage 131 by movement of the reactant chamber plug 112.

Particularly, because organic or biomaterials are more stable in a dried state, the reactant 113 can be stored for a long period of time without losing its activity when it is stored in a dried state in the sample chamber 110 or the reactant chamber 160. For example, the reactant 113 can be dried after its absorption into fiber.

In addition, the reaction chamber may further comprise, above the dried reactant 114, a solvent 115 for dissolving the dried reactant 114.

In addition, the analyte detection device of the present invention may further comprise a buffer chamber. Herein, the buffer chamber may be connected between the sample chamber 110 and the detection chamber 120, or between the sample chamber 110 and the labeling chamber 140, or between the labeling chamber 140 and the detection chamber 120.

Particularly, why the buffer chamber is disposed is because, when the channel 130 is filled with a washing buffer, the washing buffer can be diffused to and mixed with other solution during storage of the analyte detection device 100. Thus, it is preferred that the channel 130 be filled with air, and then filled with a washing buffer when the analyte detection device 100 is used.

In addition, the buffer chamber may be connected to the channel 130 through a second connection passage 132, and the diameter of the second connection passage 132 may be smaller than that of each of the buffer chamber and the sample chamber 110.

Herein, the buffer chamfer comprises a second cavity formed therein, and a buffer chamber plug 112 disposed in the upper portion of the second cavity so as to be movable up and down by external pressure, wherein the buffer is contained in the lower portion of the second cavity so that it will be discharged to the sample chamber 110 through the second connection passage 132 and the channel 130 by up-and-down movement of the buffer chamber plug.

Furthermore, the analyte detection device 100 of the present invention may comprise a fixing cover 170. More specifically, the analyte detection device 100 comprises: a fixing cover 170 provided at the top of the analyte detection device 100; a first, protrusion 171 formed on the fixing cover 170 at a position corresponding to the reactant chamber plug 112; and a second protrusion 171 formed on the fixing cover 170 at a position corresponding to the buffer chamber plug, wherein the first protrusion 171 and the second protrusion 171 can move the reactant chamber plug 112 and the buffer chamber plug downward by external pressure. In a specific embodiment, the analyte detection device 100 may further comprise, in the fixing cover 170, a sample inlet 111 for injecting a sample.

In addition, the reactant 113 may also be stored in the sample chamber without being stored in a separate reactant chamber 160. In this case, the reactant 113 may be a dried reactant 114, and the dried reactant 114 may be obtained by absorbing a liquid-state reactant into a liter substrate and drying the absorbed reactant.

In a specific embodiment, the receptor may be a primary receptor capable of binding directly to the analyte 210. More specifically, if the analyte 210 is one of substances such as proteins, organic molecules, viruses, bacteria, plant cells or animal cells, for which antibodies can be formed, an antibody for each analyte 210 may be used as the receptor. As an example, if the analyte 210 is lectin, a carbohydrate may be used as the receptor, and on the contrary, if the analyte 210 comprises a carbohydrate, lectin may be used as the receptor. As another example, if the analyte 210 is nucleic acid such as DNA or RNA, a DNA or PNA (peptide nucleic acid) having a nucleotide sequence complementary thereto may be used as the receptor. In addition, any substances, including aptamers obtained from nucleic acids, peptide ligands obtained from peptide libraries, protein ligands obtained from affibody libraries, etc., may be used as the receptor, as long as the analyte 210 may bind specifically thereto.

In another specific embodiment, the receptor may be a secondary receptor capable of binding to the primary receptor, and the primary receptor may be a receptor capable of binding directly to the analyte 210. More specifically, if the primary receptor is an antibody, the secondary receptor used may be a secondary antibody or protein G. As another example, if the primary receptor is DNA or PNA (peptide nucleic acid), a DNA or PNA complementary to a portion of the nucleotide sequence of the primary receptor may be used as the secondary receptor.

Herein, the secondary antibody used may be, for example, an anti-rabbit immunoglobulin G antibody, if the primary antibody is of rabbit origin.

In another specific embodiment, the receptor may be a receptor capable of binding to a substance produced by the analyte 210, and the analyte 210 may be an enzyme. More specifically, the receptor may be a receptor for a substance that is produced in proportion to the amount of the analyte 210. For example, if the analyte 210 is an enzyme, the receptor may be a receptor for the product. As another example, a receptor for a molecule that is dissociated or structurally changed in response to the analyte 210 may also be used.

The analyte detection device 100 of the present invention is characterized in that the particles 200 are moved from the sample chamber 110 to the detection chamber 120 by moving means. Herein, the moving means may be a centrifugal force, gravity, or a magnetic force.

In addition, the particles 200 may be composed of two or more types of particles. For example, the particles 200 may be composed of magnetic particles and nonmagnetic particles, or may composed of particles having a specific gravity lower than that of the detection solution and particles having a specific gravity higher than that of the detection solution. In a specific embodiment, a centrifugal force and a magnetic force may be used together to move the two or more types of particles. This will be described in detail later.

The analyte detection device 100 of the present invention may comprise at least one vibrating unit in order to react a sample with the reactant 113 or to promote movement of the particles 200. The vibrating unit may be a vibrator.

In addition, a suitable label function is required for detection. The label is not specifically limited, as long as it includes measurable properties, including magnetic properties, optical properties such as fluorescence, luminescence or absorbance, catalytic activities such as enzymes or metal catalysts, radioactivity, electrical conductivity, mass, and the like.

In a specific embodiment, catalytic activity may serve as a label. If catalytic activity serves as a label, the production or dissipation of a fluorescent product, the production or dissipation of a light-absorbing substance, the generation of light, a change in pH, a change in electrical conductivity, a change in potential difference, a change in mass, or the like, which results from the catalytic reaction, may be measured.

In another specific embodiment, a light-absorbing property may serve as a label. In this case, two opposite sides in the detection chamber are preferably transparent in order to measure; absorbance. In addition, if luminescence that is light emission serves as a label, one side of the detection chamber may be transparent, and the remaining sides of the detection chamber may be white or silver in color so that they can more easily reflect light.

In another specific embodiment, fluorescence may serve as a label. In this case, one side of the detection chamber 120 may be transparent, and the remaining sides of the detection chamber 120 may be black in color so that they can easily absorb light. Alternatively, the two non-opposite sides of the detection chamber 120 may be transparent, and the remaining sides may be black in color so that they can easily absorb light.

Methods for detecting the analyte 210 using the analyte detection device 100 as described above are as follows.

Specifically, the present invention is directed to a method for detecting an analyte using the analyte detection device 100, the analyte detection device 100 comprising: a sample chamber 110 configured to contain a mixed solution of a reactant 113 comprising the particles 200 and a sample containing the analyte 210; a detection chamber 120 configured to contain a detection solution; and a channel 130 located between the sample chamber 110 and the detection chamber 120 so as to prevent the mixed solution and the detection solution from mixing with each other; the method comprising the steps of: mixing and reacting the sample containing the analyte 210 with the reactant 113 comprising the particles 200 in the sample chamfer 110; moving the particles 200 to the detection chamber 120 by moving means; and detecting the analyte 210 in the detection chamber 120.

The present invention is also directed to a method for detecting an analyte using the analyte detection device 100, the analyte detection device 100 comprising: a sample chamber 110 configured to contain a mixed solution of a reactant comprising capture particles 200 and labeling particles 250 and a sample containing the analyte 210; a detection chamber 120 configured to contain a detection solution; and a channel 130 located between the sample chamber 110 and the detection chamber 120 so as to prevent the mixed solution and the detection solution from, mixing with each other; the method comprising the steps of: mixing the reactant 113 and the sample in the sample chamber 110 to form a capture particle-analyte-labeling particle conjugate; moving the capture particle-analyte-labeling particle conjugate to the detection chamber 120 by moving means; and detecting the analyte 210 in the detection chamber 120.

Herein, the capture particles 220 may be magnetic particles having immobilized thereon a primary receptor specific for the analyte 210, and the labeling particles 250 may be nonmagnetic particles having the primary receptor specific for the analyte 210 and comprising a label.

In another embodiment, the capture particles 220 may be particles having immobilized thereon a primary receptor specific for the analyte 210 and having a specific gravity greater than that of the detection solution, and the labeling particles may be particles having immobilized thereon the primary receptor specific for the analyte 210 and comprising a label and having a specific gravity smaller than that of the detection solution.

The receptors that are immobilized on the capture particles 220 and the labeling particles 250 may be the same primary receptor or may be two kinds of primary receptors that bind to different sites. In other words, the first receptor and the second receptor may also be used.

Herein, the analyte 210 may be at least one selected from among viruses, bacteria, and eukaryotic cells, which have a plurality of binding sites.

The present invention is also directed to a method for detecting an analyte using the analyte detection device 100, the analyte detection device 100 comprising: a sample chamber 110 configured to contain a mixed solution of a sample containing the analyte 210 and a reactant 113 comprising capture particles 220 having immobilized thereon a primary receptor specific for the analyte 210 and a standard material having a label attached thereto; a detection chamber 120 configured to contain a detection solution; and a channel 130 located between the sample chamber 110 and the detection chamber 120 so as to prevent the mixed solution and the detection solution from mixing with each other; the method comprising the steps of: mixing the reactant 113 and the sample in the sample chamber 110 to form a capture particle-analyte complex and a capture particle-standard material complex; moving the capture particle-analyte complex and the capture particle-standard material complex to the detection chamber 120 by moving means; and detecting the analyte in the detection chamber 120 by use of the label linked to the standard material, wherein the standard material is capable to the primary receptor competitively with the analyte 210.

The present invention is also directed to a method for detecting an analyte using the analyte detection device 100, the analyte detection device 100 comprising: a sample chamber 110 configured to contain a mixed solution of a sample containing the analyte 210 and a reactant comprising capture particles 220 having immobilized thereon a primary receptor specific for the analyte 210 and a secondary receptor specific for the primary receptor, and a labeled receptor 230 having a label attached thereto; a detection chamber 120 configured to contain a detection solution; and a channel 130 located between the sample chamber 110 and the detection chamber 120 so as to prevent the mixed solution and the detection solution from mixing with each other; the method comprising the steps of: mixing the reactant 113 and the sample in the sample chamber 110 to form a capture particle-primary receptor-analyte complex and a capture particle-primary receptor-standard material complex; moving the capture particle-primary receptor-analyte complex and the capture particle-primary receptor-standard material complex to the detection chamber 120 by moving means; and detecting the analyte in the detection chamber 120 by use of the label linked to the standard material wherein the standard material is capable of bind to the primary receptor competitively with the analyte 210. Herein, the analyte 210 may be at least one selected from among organic toxins, antibiotics and narcotics.

The present invention is also directed to a method for detecting an analyte using the analyte detection device 100, the analyte detection device 100 comprising: a sample chamber 110 configured to contain a mixed solution of a sample containing the analyte 210 and a reactant 113 comprising a capture particles having immobilized thereon a first receptor specific for the analyte 210 and a labeled receptor 230 comprising a label attached to a second receptor specific for the analyte 210; a detection chamber 120 configured to contain a detection solution; and a channel 130 located between the sample chamber 110 and the detection chamber 120 so as to prevent the mixed solution and the detection solution from mixing with each other; the method comprising the steps of: mixing the reactant 113 and the sample in the sample chamber 110 to form a capture particle-analyte-labeled receptor complex; moving the capture particleanalyte-labeled receptor complex to the detection chamber 120 by moving means; and detecting the analyte 210 in the detection chamber 120 by use of the label attached to the labeled receptor, wherein the first receptor and the second receptor are capable to bind non-competitively to different sites of the analyte 210. Herein, the analyte 210 may be at least one selected from among proteins, nucleic acids and carbohydrates.

As shown in FIG. 8, the present invention is directed to a system 300 for detecting an analyte using gravity, the system 300 comprising: an analyte detection device comprising a sample chamber 110 configured to contain a mixed solution of a reactant 113 comprising particles 200 and a sample containing the analyte, a detection chamber 120 disposed below the sample chamber and configured to contain a detection solution, and a channel 130 located between the sample chamber 110 and the detection chamber 120 so as to prevent the mixed solution and the detection solution from mixing with each other; and at least one valve 310 between the sample chamber 110 and the channel 130, wherein the particles 200 have a specific gravity greater than that of each of the mixed solution and the detection solution. Herein, at least one selected from the group consisting of glycerol, sugar and Ficoll may be added to the detection solution in order to increase the specific gravity of the detection solution.

In addition, the present invention is directed to a method for detecting an analyte using gravity, which uses the system 300 for detecting the analyte using gravity and comprises the steps of: reacting the reactant 113 with the sample in the sample chamber 110 in a state in which the valve 310 is closet; opening the valve 310 to move the particles 200 to the detection chamber 120; and detecting the analyte in the detection chamber 120. For example, the channel 130 is made of a soft tube, the channel 130 can be simply closed using a clamp 452, and the stopcock-type valve 310 may also be disposed. Particularly, when the analyte is to be detected; using gravity, the particles 200 used can be heavy so that they can precipitate in the sample or the detection solution.

In another embodiment as shown in FIG. 9, a system for detecting an analyte 210 using gravity according to the present invention comprises an analyte detection device 100 comprising: a sample chamber 110 configured to contain a mixed solution of a reactant 113 comprising particles 200 and a sample containing the analyte 210; a detection chamber 120 configured to contain a detection solution; and a channel 130 located between the sample chamber 110 and the detection chamber 120 so as to prevent the mixed solution and the detection solution from mixing with each other, wherein the channel 130 is configured to connect the upper portion of the sample chamber 110 with the upper portion of the detection chamber 120 in a state in which the sample chamber 110 and the detection chamber 120 are horizontally positioned, and the particles 200 have a specific gravity greater than that of each of the mixed solution and the detection solution. In this case, at least one selected from the group consisting of glycerol, sugar and Ficoll may be added to the detection solution in order to increase the specific gravity of the detection solution.

A method for detecting an analyte using the system 300 for detecting the analyte using gravity comprises the steps of: reacting the reactant 113 with the sample in the sample chamber 110; inclining the analyte detection device 100 at an angle of 20-70° such that the channel 130 faces downward, thereby moving the particles 200 to the detection chamber 120; and detecting the analyte in the detection chamber 120.

The method for detecting an analyte using gravity according to the embodiment of the present invention has advantages in that it does not require a separate device to move the particles 200, and thus is highly economical and is conveniently used on site.

In addition, as shown in FIGS. 10 and 11, the present invention is directed to a system 400 for detecting an analyte using a centrifugal force, the system 400 comprising: an analyte detection device comprising a sample chamber 110 configured to contain a mixed solution of a reactant 113 comprising particles 200 and a sample containing an analyte 210, a detection chamber 120 configured to contain a detecting solution, and a channel 130 located between the sample chamber 110 and the detection chamber 120 so as to prevent the mixed solution and the detection from mixing with each other; a disc 410 which includes a plurality of the analyte detection devices 100 and is rotatable; and at least, one detector 420 located near the disc 410, wherein the detection chamber 120 is disposed outward from the center of the disc 410.

Herein, the channel 130 may comprise a single valve 440. As shown in FIG. 12, the valve 440 comprises a rotatable shaft configured, to open or close the channel 130, and a weight connected to the rotatable shaft. The weight can be rotated by a centrifugal force caused by rotation of the disc 410, thereby opening the channel 130.

In another embodiment, as shown in FIG. 13, the valve 450 comprises a valve body 451, and a clamp 452 located on the valve body 451 so as to open or close the channel 130. Herein, the clamp 452 is movable horizontally by rotation of the disc 410 to thereby open the channel 130.

In this embodiment, the particles 200 may have a specific gravity greater than that of each of the mixed solution comprising the sample and the detection solution.

The present invention is also directed to a method for detecting an analyte using a centrifugal force, which uses the system 400 for detecting the analyte using a centrifugal force and comprises the steps of: reacting the reactant 113 and the sample in the sample chamber 110; rotating the disc 410 to open the valve 440 or 450 to thereby open the channel 130; moving the particles 200 to the detection chamber 120; and stopping the rotation, and then rotating the disc 410 at an angle of 10-180° such that the detection chambers 120 of the detection devices sequentially face the detector 420, thereby detecting the analyte in the detection chamber 120.

As an example, eight analyte detection devices 100 may be disposed in the disc 410. In this case, the analyte 210 in the detection chamber 120 can be analyzed by the single detector 420 while the disc 410 is rotated at an angle of 45°.

Particularly, the moving speed of the particles 200 toward the detection chamber 120 can be controlled according to the rotating speed of the disc 410. Herein, the particles 200 may be a particle-analyte complex. Additionally, the sample may contain solid dregs, and thus when the mixed solution containing the sample is likely to move to the detection chamber 120 or to be mixed with the detection solution due to the high specific gravity of the mixed solution containing the sample, a substance, such as glycerol, sugar, Ficoll or the like, which increases specific gravity, may be added to the detection solution. In addition, a filter 520 for filtering dregs may be disposed in the sample inlet.

In particular, if the analyte 200 is in the form of particles 200 such as bacteria, the analyte 210 can be detected by the method for detecting the analyte 210 using the centrifugal force according to the present invention without using separate particles 200. For example, when the labeled receptor 230 having a function of labeling a receptor for bacteria is bound to bacteria and then a centrifugal force is applied thereto, only a bacteria-labeled receptor complex can move to the detection chamber 120, and thus the number of the bacteria can be evaluated by measuring the signal of the label in the detection chamber 120.

Herein, in order to increase sensitivity, particles 200 having low buoyant density may be labeled, and a receptor for bacteria may be immobilized on the particles 200. For example, polystyrene nanoparticles having a size of several tens of nanometers have a specific gravity of about 1.0 and a small size, and thus are not easily settled down by the centrifugal force. Where a receptor is immobilized on such light particles which are then labeled, the particles are referred to as the labeling particles 250, because these particles do not contribute to movement. When the labeling particles 250 are mixed and reacted with a sample and a centrifugal force is applied thereto, labeling particles 250 unbound to bacteria will not move, and only a complex comprising the labeling particles 250 bound to bacteria will move to the detection chamber 120, and thus the number of the bacteria can be evaluated by measuring the signal of the label in the detection chamber 120.

As shown in FIGS. 14 and 15, the present invention is directed to a system for detecting an analyte using a magnetic force, comprising: an analyte detection device comprising a sample chamber 110 configured to contain a mixed solution of a reactant 113 comprising magnetic particles and a sample containing an analyte 210, a detection chamber 120 configured to contain a detection solution, and a channel 130 located between the sample chamber 110 and the detection chamber 120 so as to prevent the mixed solution and the detection solution from mixing with each other; and at least one magnetic force application unit 510 disposed on the outer wall of the analyte detection device 100 and configured to apply a magnetic force to the magnetic particles 250, wherein the sample chamber 110 and the detection chamber 120 are horizontally disposed.

The present invention is also directed to a method for detecting an analyte using a magnetic force, which uses the system for detecting the analyte using the magnetic force and comprises the steps of: reacting the reactant 113 with the sample in the sample chamber 110; applying a magnetic force from the detection chamber 120 to the sample chamber 110 using a magnetic force application unit 510 disposed on one side of the detection chamber 120, thereby moving the magnetic particles from the sample chamber 110 to the detection chamber 120; and detecting the analyte in the detection chamber 120.

In another embodiment, the present invention is directed to a method for detecting an analyte using a magnetic force, which uses the system for detecting the analyte using the magnetic force and comprises the steps of: reacting the reactant 113 with the sample in the sample chamber 110; moving the magnetic force application unit 510, located on the outside of the analyte detection device 100, from the sample chamber 110 to the detection chamber, thereby moving the magnetic particles from the sample chamber 110 to the detection chamber 120; and detecting the analyte 210 in the detection chamber 120.

In the method for detecting the analyte 210 using the magnetic force as described above, the position of the magnetic particles is determined by the position of the magnetic force application unit, and thus the moving direction or moving speed of the magnetic particles 250 can be easily controlled.

In addition, when the particles 200 are moved by the magnetic force, the particles 200 move along the wall surface of the device 100 for detecting the analyte 210. For this reason, in order to facilitate the movement of the particles 200, at least one surface of the device 100 for detecting the analyte 210 should be smooth without irregularities. In addition, because it is easy to move the particles 200 along the bottom surface, due to gravity, the sample chamber 110, the channel 130 and the detection chamber 120 may be horizontally disposed and the channel 130 may be configured to connect the lower portion of the sample chamber 110 with the lower portion of the detection chamber 120.

Particularly, based on the fact that bacteria have several binding sites, the bacteria can be detected using two kinds of particles 200 having different properties. More specifically, only a receptor for bacteria may be immobilized on the magnetic particles so that the particles can be used as capture particles 220, and a receptor for bacteria may be immobilized on other nonmagnetic particles which are then labeled so that the nonmagnetic particles can be used as labeling particles 250.

Herein, the receptors that are immobilized on two kinds of particles may be the same receptor, but may also be two kinds of receptors that bind to different sites. When two kinds of particles as described above are mixed and reacted with the sample, all the two kinds of particles bind to bacteria. Then, when the particles are moved using a magnetic force, as shown in FIG. 17, the capture particles 220 move to the deletion chambers 220. Herein, if the capture particles 220 have bacteria bound thereto, the labeling particles 250 can also bind to the bacteria. However, because labeling particles 250 unbound to bacteria do not move to the detection chamber 120, the number of the bacteria can be evaluated by measuring the label signal of the bacteria-bound labeling particles 250 that moved to the detection chamber 120.

The above-described method that uses two kinds of particles having different properties may applied to, in addition to bacteria, any analytes having several binding sites, such as cells or viruses.

A system for n the analyte 210 using a magnetic force according to the present invention comprises: an analyte detection device 100 comprising a sample chamber 110 configured to a mixed solution of a sample containing the analyte 210 and a reactant 113 comprising labeling capture particles 240 which have a label attached to magnetic particles and have immobilized thereon a receptor for the analyte, a detection chamber 120 configured to contain a detection solution, and a channel 130 located between the sample chamber 110 and the detection chamber 120 so as to prevent the mixed solution and the detection solution from mixing with each other; a filter 520 disposed on the bottom inside the analyte detection device 100; and at least one magnetic force application unit 510 disposed on the outer wall of the bottom of the analyte detection device 100 and configured to apply a magnetic force to the labeling capture particles 240, wherein the channel 130 is configured to connect the bottom of the sample chamber 110 with the bottom of the detection chamber 120 in a state in which the sample chamber 110 and the detection chamber 120 are horizontally disposed.

In addition, the system may further comprise a porous filter 520 support for supporting the filter 520, and the filter 520 may be a filter capable of filtering the magnetic particles 250. Furthermore, the filter 520 may be a filter through which labeling capture particles 240 unbound to the analyte 210 pass and a labeling capture particle-analyte complex does not pass. Moreover, the filter 520 may be negatively or positively charged.

As shown in FIG. 18, the present invention is directed to a method for detecting an analyte using a magnetic force, which uses the system for detecting the analyte using the magnetic force and comprises the steps of: reacting the reacting the reactant 113 with the sample in the sample chamber 110 to form a labeling capture particle-analyte complex; moving the magnetic force application unit 510 from the sample chamber 110 to the detection chamber 120, thereby discharging labeling capture particles 240 unbound to the analyte 210 and moving the labeling capture particle-analyte complex to the detection chamber 120; and detecting the analyte 210 in the detection chamber 120 by use of the label attached to the labeling capture particles 240.

The present invention is also directed to a system for detecting an analyte using a magnetic force and a centrifugal force, which comprises an analyte detection device 100 comprising a sample chamber 110 configured to contain a mixed solution of a sample containing the analyte 210 and a reactant 113 comprising labeling capture particles 240 which have a label attached thereto and have immobilized thereon a receptor for the analyte 210, a detection chamber 120 configured to contain a detection solution, and a channel 130 located between the sample chamber 110 and the detection chamber 120 so as to prevent the mixing solution and the detection solution from mixing with each other; a filter 520 disposed on the bottom inside the analyte detection device 100; at least one magnetic force application unit 510 disposed on the outer wall of the bottom of the analyte detection device 100 and configured to apply a magnetic force to the labeling capture particles 240; a disc 410 which includes a plurality of the analyte detection devices 100 and is rotatable; and at least one detector 420 located near the disc 410, wherein the sample chamber 110 is disposed toward the center of the disc 410, and the detection chamber 120 is disposal outward from the center of the disc 410, and the channel 130 is configured to connect the bottom of the sample chamber 110 with the bottom of the detection chamber 120.

Herein, the filter 520 may be a filter 520 through which labeling capture particles 240 unbound to the analyte 210 pass and the labeling capture particle-analyte complex does not pass.

In addition, as shown in FIG. 19, the present invention is also directed to a method for detecting an analyte using a magnetic force and a centrifugal force, which uses the system for detecting the analyte using the magnetic force and the centrifugal force and comprises the steps of: reacting the reactant 113 with the sample in the sample chamber 110 to form a labeling capture particle-analyte complex; rotating the disc 410 in a state in which the magnetic force application unit 510 is fixed to the bottom of the sample chamber 110, thereby discharging labeling capture particles 240 unbound to the analyte 210 to the bottom of the filter 520 and moving the labeling capture particle-analyte complex to the detection chamber 120; and detecting the analyte in the detection chamber 120 by use of the label attached to the labeling capture particles 240.

In addition, when a high-molecular-weight substance such as a protein, a nucleic acid, a carbohydrate or the like is to be detected it can be detected by a sandwich method using two kinds of receptors (i.e., the first receptor and the second receptor) that are capable of simultaneously binding non-competitively to different sites of the analyte (see FIGS. 2 and 3).

The sandwich method is performed using an analyte detection device comprising: a sample chamber configured to contain a mixed solution of a sample containing an analyte and a reactant comprising capture particles 220 having immobilized thereon a first, receptor specific for the analyte and a labeled receptor 230 having a label attached to a second receptor specific for the analyte; a detection, chamber configured to contain a detection solution; and a channel located between the sample chamber and the detection chamber so as to prevent the mixed solution and the detection solution from mixing with each other. The sandwich method uses the analyte detection device, and comprises the steps of: mixing the reactant and the sample in the sample chamber to form a capture particle-analyte-labeled receptor complex; moving the capture particle-analyte-labeled receptor complex to the detection chamber by moving means; and detecting the analyte by use of the label attached to the labeled receptor (FIG. 20).

When the device of FIG. 2 is used, a sample containing an analyte is reacted only with capture particles 220 in the sample chamber to form a capture particle-analyte complex, and then the particles are moved to the labeling chamber. In the labeling chamber, a labeled receptor is additionally bound to the capture particle-analyte complex to form a capture particle-analyte-labeled receptor complex. Finally, the capture particle-analyte-labeled receptor complex is moved to the detection chamber, and then the analyte can be detected using the labeling function of the labeled receptor.

In addition, it is also possible to detect an analyte using capture particles 220 and labeling particles 250 as two kinds of particles having different properties, as described above with respect to the detection of bacteria. In this case, however, different receptors, that is, the first receptor and the second receptor, should be immobilized on the two kinds of particles.

To detect low-molecular-weight substances such as organic toxins, narcotics, antibiotics or the like, a competitive immunoassay is used, because it is difficult to make two kinds of antibodies that bind to different sites. In this competitive immunoassay method, a receptor is immobilized on particles 200 to make capture particles, and a standard material for the analyte is labeled to make a labeled standard material. Herein, "standard material for the analyte 210" means either an analyte 210 which has already been purified to have a known concentration, or a material capable of binding to a receptor for the analyte 210, and refers to a material that can be used as a standard for evaluating the amount of the analyte contained in the sample. When capture particles and a labeled standard material is added to and reacted with a sample containing the analyte 210, the labeled standard material will bind to the capture particles in an amount inversely proportional to the amount of the analyte 210 contained in the sample. Thus, the amount of the analyte 210 can be evaluated by moving the capture particles to the detection chamber and measuring the signal of the label bound to the capture particles.

In the competitive immunoassay, a second receptor may also be immobilized instead of immobilizing the receptor for the analyte 210 on the particles 200. If the primary receptor is an antibody, a secondary antibody or protein G may be used as the secondary receptor. In the case in which the secondary receptor is immobilized on the capture particles, the capture particles, the primary receptor for the analyte 210, and the labeled standard are added to and reacted with the sample, after which the particles 200 are moved.

In the competitive immunoassay, the standard material for the analyte 210 may also be immobilized on the particles 200 to make capture particles instead of immobilizing the receptor on the particles 200. In this case, the receptor should be labeled to make a labeled receptor 230. When the capture particles having the standard material immobilized thereon and the labeled receptor 230 are added to and reacted with the sample, the labeled receptor 230 will bind to the capture particles in an amount inversely proportional to the amount of the analyte contained in the sample. Thus, the amount of the analyte 210 can be evaluated by moving the particles to the detection chamber and measuring the signal of the label bound to the particles 200.

In addition according to the present invention, the amount of the analyte 210 can be evaluated by detecting a material that is produced in proportional to the amount of the analyte 210. In this case, a receptor for the material that is produced in the amount of the analyte 210 should be immobilized on the particles 200, and if the analyte 210 is an enzyme, the receptor may be a receptor for the product of the enzyme. Alternatively, a receptor for a molecule that is dissociated or structurally changed in response to the analyte 210 may also be immobilized on the particles 200. Where the receptor for the product is immobilized on the particles 200, the product itself preferably has a labeling function. Where the receptor for the molecule that is dissociated or structurally changed in response to the analyte 210 is immobilized on the particles, the molecule may be labeled.

As shown in FIG. 21, examples of detachable materials that are produced in the amount of the analyte 210 include kinase enzyme.

Herein, kinase has an activity of phosphorylating its substrate protein, and antibodies are known, which do not bind to unphosphorylated substrate proteins and can bind only to phosphorylated substrate proteins. Thus, when the substrate protein is labeled and the receptor capable of binding only to the phosphorylated substrate protein is immobilized to the particles 200, the amount of kinase in the sample can be measured.

As shown in FIG. 22, examples of detectable materials that are dissociated in response to the analyte 210 include protease.

For example, a material capable of functioning as a label is immobilized on a stationary solid phase using a peptide, which can act as a substrate for protease, as a linker. Herein, the stationary solid phase can be the sample chamber wall or a stationary particle. In addition, a receptor for the label material is immobilized on movable particles to make capture particles. When the peptide is cleaved by action of protease, the label material will be dissociated from the stationary solid phase, and thus the label material will bind to the receptor on the particles 200 and move to the detection chamber.

In particular, the present invention can be used to detect analytes 210, including organic materials, proteins, nucleic acids, cells, or the like.

Hereinafter, the present invention will be described in detail with reference to experimental examples in order to assist in the understanding of the present invention. It is to be understood, however, that these experimental examples are for illustrative purposes only and are not intended to limit the scope of the present invention. The experimental examples of the present invention are provided to more fully convey the disclosure of the present invention to those skilled in the art.

EXPERIMENTAL EXAMPLES

Experimental Example 1

Detection of Paralytic Shellfish Poison by Method of Moving Particles by Centrifugal Force In this Experimental Example, in order to detect paralytic shellfish toxin (PST) by a method of moving particles 200 by a centrifugal force, paralytic shellfish toxin was detected by a competitive immunoassay according to the principle shown in FIG. 23.

Paralytic shellfish toxin (PST) is composed of various toxins, and an antibody (STX Ab) against saxitoxin (STX) that is the most important toxin among the toxins was used as a primary antibody. As a solid phase, magnetic particles 250 (G-MB, Pierce, USA) having protein G immobilized thereon were used. Particularly, the protein G acted as a secondary receptor capable of binding to the antibody. In addition, as a labeled standard material to react competitively with the toxin contained in the sample, horseradish peroxidase (HRP)-conjugated STX (STX-HRP) was used. Further, STX Ab solution and STX-HRP solution were purchased from Beacon Analytical Systems (USA) and used without changes. ABTS solution (Sigma), a substrate for HRP, was filled in a (Motion chamber 120 and used as a detection solution.

When a reactant 113 comprising STX-HRP, STX Ab and G-MB was mixed and reacted with the sample in the sample chamber 110, STX Ab did bind to G-MB, and the toxin contained in the sample and STX-HRP competitively reacted with STX Ab. After completion of the reaction, G-MB was moved to the detection chamber 120, and then a color appeared due to the enzymatic activity of STX-HRP bound to G-MB (FIG. 23). Herein, as the toxin concentration of the sample increased, the amount of STX-HRP bound to G-MB decreased, and thus the absorbance of the detection solution decreased.

In order to make a detection device in which the particles 200 are moved by a centrifugal force, a 2-way stopcock (purchased from Bio-Rad) for syringe use was connected to a immunoplate well (purchased from Corning) using a silicon tube, and a 3 ml syringe was then connected thereto (FIG. 24). Herein, the immunoplate well serves as the detection chamber, the syringe serves as the sample chamber, and the 2-way stopcock serves as the channel 130.

First ABTS solution was filled from the immunoplate well up to the valve 310 of the 2-way stopcock, and the valve 310 was closed, 50 µl of STX Ab solution, 50 µl of STX-HRP solution, 50 µl of a sample containing STX, 30 µl of G-MB and 320 µl of PBS buffer were placed in the syringe and reacted for 30 minutes with shaking. The syringe was carefully put into the 2-way stopcock such that no bubbles would be formed in the middle portion of the 2-way stopcock, and swinging bucket. Then, the syringe was centrifuged in a centrifuge equipped with a swinging bucket at 1000 rpm for 5 minutes. Finally, the immunoplate well was separated, and the absorbance at 405 nm was measured with a microplate reader.

As a result, as can be seen in FIG. 25, as the concentration of STX increased, the absorbance decreased, indicating that the competitive immunoassay was properly performed. Such results show that STX-HRP bound to the G-MB particles was moved to the detection chamber by the centrifugal force. In addition, it could be seen that STX-HRP unbound to the G-MB particles did not move to the detection chamber, indicating that no solution moved to the detection, chamber.

Experimental Example 2

Detection of Paralytic Shellfish Poison by Method of Moving Particles by Fixed Stationary Magnet In this Experimental Example, paralytic shellfish poison was detected by a method of moving the particles 200 by a fixed magnet.

The principle of a competitive immunoassay for detecting paralytic shellfish poison, and the materials used in the competitive immunoassay, were the same as those in Example 1. However, as the detection solution, Lumigen PS-atto reagent (Lumigen) was used to measure the degree of luminescence caused by HRP enzyme.

In order to make a lab-on-a-chip (LOC) to be used in a detection device in which particles 200 are moved by a fixed magnet; a structure as shown in FIG. 26 was prepared using PDMS. The total size of this structure was 41 mm (W)×26 mm (L)×7 mm (H); the diameter of the detection chamber was 5 mm; the size of the sample chamber was 10 mm (W)×10 mm (L); and the channel 130 had a length of 10 mm, a width of 1 mm and a height of 1 mm. Glass having a thickness of 2 mm was attached to the bottom of the structure to form each chamber and the channel 130. A detection solution was placed in the detection chamber and the channel 130, and then the top of the detection chamber was sealed with a transparent tape.

The device for measurement was manufactured in a light-shieldable box as shown in FIG. 27. A photodetector and a magnet were disposed above and below an LOC holder, respectively, such that the photodetector and the magnet were located immediately above and below the detection chamber of the LOC when the LOC was introduced. The LOC holder was disposed above a vibrator.

50 μl of STX Ab solution, 50 μl of STX-HRP solution, 50 μl of a sample containing STX, 10 μl of G-MB, and 60 μl of BSA-PBS (0.1% BSA-containing PBS buffer) were placed in a microtube and reacted for 30 minutes. The reaction mixture was placed in the sample chamber of the LOC, and then the top of the sample chamber was sealed with a transparent tape.

The LOC was placed in the measurement device, and the box was covered with a lid. In this state, the intensity of light detected by the photodetector was measured while vibration was applied. As a result, as shown, in FIG. 28(A), the intensity of light increased progressively with time, and the rate of the increase was inversely proportional to the concentration of STX contained in the sample. FIG. 28(B) shows the intensity of light as a function of the concentration of STX contained in the sample.

The above results show that, when the magnet is fixed to the bottom of the detection chamber and vibration is applied to the LOC, the magnetic particles 250 can be moved from the sample chamber to the detection chamber, and STX-HRP unbound to the magnetic particles 250 does not move from the sample chamber to the detection chamber.

Experimental Example 3

Detection of Paralytic Shellfish Poison by Method of Moving Particles by Movement of Magnet In this Experimental Example, paralytic shellfish poison was detected by a method of moving particles by movement of a magnet.

The principle of a competitive immunoassay for detecting paralytic shellfish poison, and the materials used in the competitive immunoassay, were the same as those in Example 1. However, as the detection solution, ABTS solution, was used to measure the degree of color development caused by HRP enzyme.

A structure for manufacturing a lab-on-a-chip (LOC) was manufactured as shown in FIG. 29 by slightly modifying the structure of Example 2. In order to facilitate mixing by shaking, the shape of the detection chamber was changed to a rectangular shape (5 mm×10 mm), and in order to prevent a solution in the sample chamber and a solution in the detection chamber from mixing with each other, the length of the channel 130 was made longer (15 mm), and each of the width and height of the channel 130 were made smaller (0.5 mm). The total size of the LOC was also made smaller (41 mm (W)×20 mm (L)×5 mm (H)).

In addition, a device for moving magnetic particles 250 was manufactured using a syringe pump as shown in FIG. 30. A vibrator was fixed to one end of the pump, and an LOC holder was disposed thereon. A magnet was fixed to the moving portion of the pump so as to be located on the bottom of each LOC. Also, when the moving portion of the pump moved, each magnet moved from the sample chamber of each LOC to the detection chamber. In addition, vibration was applied during movement of the magnet so that the magnetic particles 250 would effectively move.

First, an experiment was performed to examine whether or not a solution in the sample chamber of the LOC is mixed with a solution of the detection chamber and whether or not other materials of the sample chamber also move when particles 200 are moved. The detection chamber and the channel 130 in each of two LOCs were filled with 150 μl of BSA-PBS, and the top of the detection chamber was sealed with a transparent tape. To the sample chamber, 10 μl (10 μl) of G-MB, 109 μl of BSA-PBS, 100 μl of HRP-conjugated anti-rabbit immunoglobulin antibody (HRP-Ab, Sigma; diluted at 1:10,000), and 0.1 μg (10 μl) were added. After the top side of the sample chamber was closed with a tape, the mixture was allowed to react for 30 minutes while it was shaken at 350 rpm. Herein, HRP-Ab did bind to G-MB, but HRP remained in the solution without binding. In one of the two LOCs, the magnetic particles 250 were not moved, and the solution of the sample chamber and the solution of the detection chamber were taken and transferred to microtubes. In the case of the remaining LOC, the magnet was moved from the bottom of the sample chamber to the bottom of the detection chamber at a speed of 2 cm/min, thereby moving the magnetic particles 250. The solutions in the two chambers were also taken and transferred to microtubes. The magnetic particles 250 were recovered from the four solutions, and then the activity of HRP enzyme remaining in the solutions and the activity of HRP enzyme present on the magnetic particles 250 were measured.

As a result as shown in FIG. 31, the magnetic particles 250 were present only in the sample chamber before moment of the magnet (SC-MB, light pay color) and were not present in the detection chamber (DC-MB, light gray color). However, after movement of the magnet, it could be seen that the magnetic particles 250 did not remain in the sample chamber (SC-MB, dark gray color) and were present in the detection chamber (DC-MB, dark gray color). This suggests that the magnetic particles 250 remained in the sample chamber without moving to the detection chamber during the first 30 minutes of shaking, and then were moved to the detection chamber by movement of the magnet. In addition, the activity of HRP enzyme in the solutions was found only in the sample chamber before or after movement of the magnet (SC-sol; light gray color and dark gray color). However, the activity of HRP enzyme in the solution of the detection chamber was not substantially observed before or after movement of the magnet (DC-sol, light gray color and dark gray color). This suggests that HRP in the solution, which did not bind to the magnetic particles 250, did not move during 30 minutes of shaking and were also not moved by movement of the magnet. In conclusion, it could be seen through this experiment that the two chambers were very effectively separated from each other and only the materials bound to the magnetic particles 250 could be moved by movement of the magnetic particles 250.

Next GTX 2&3, a kind of paralytic shellfish poison, was detected using this system. Because GTX 2&3 can bind to STX-Ab due to its structure similar to that of STX, it could be detected by the same competitive immunoassay. The detection chamber and channel 130 of the LOC were filled with 150 µl of a solution of 3,3',5,5'-Tetramethylbenzidine (TMB) that is a color development substrate for HRP enzyme. This solution was purchased from Sigma. The top side of the detection chamber was sealed with a transparent tape, and 20 µg of G-MB, 75 µl of STX-Ab, 75 µl of STX-HRP, and 20 µl of a sample combining GTX 2&3 were added to the sample chamber which was then sealed with a transparent tape. The contents in the sample chamber were subjected to a binding reaction in a shaker at 350 rpm for 30 minutes, and the magnet particles 250 were moved from the sample chamber to the detection chamber by use of the magnet moving unit while vibration was applied. Next, the LOC was shaken at 350 rpm for 30 minutes so that a reaction with HRP enzyme in the detection chamber would occur. Finally, 100 µl of a solution was taken from the detection chamber and transferred to a microplate well, and then the absorbance at 600 nm was measured using a plate reader. As a result, as shown in FIG. 32, it could be seen that the absorbance was inversely proportional to the concentration of GTX 2&3, indicating that the use of this detection device enables the detection of paralytic shellfish poison.

Experimental Example 4

Detection of Bacteria by Method of Moving Particles by Movement of Magnet

In this Experimental Example, bacteria were detected by a method of moving the particles 200 by movement of a magnet.

The principle of a method for detecting bacteria using the detection device of the present invention is shown in FIG. 33. Capture particles 220 are magnetic particles having immobilized thereon an antibody specific for bacteria, and labeling particles are nonmagnetic particles having immobilized thereon an antibody specific for bacteria and an enzyme label. When the capture particles 220 and the labeling particles are added to a sample containing bacteria and allowed to react in the sample chamber, the two kinds of particles all bind to the bacteria. When the capture particles 220 are moved from the sample chamber to the detection chamber using a magnet, the bacteria bound to the capture particles 220 also move to the detection chamber. Herein, labeling particles bound to the bacteria move to the detection chamber 120 together with the bacteria, but labeling particles unbound to the bacteria remain in the sample chamber 110. Accordingly, because the amount of labeling particles that moved to the detection chamber 120 is proportional to the number of the bacteria, the number of the bacteria can be evaluated by measuring the activity of the enzyme label in the detection chamber 120.

In this Experimental Example, capture particles 220 were prepared by immobilizing biotin-anti-*Salmonella* antibody (biotin-*Salmonella* Ab; purchased from Thermo) on 1 µm-diameter Streptavidin magnetic beads (SA-MB; purchased from Dynabead). Labeling particles were prepared by immobilizing streptavidin-HRP on 100-nm-diameter COOH-silica nanoparticles (purchased from Microspheres-Nanospheres) by a chemical method using EDC, and then immobilizing biotin-*Salmonella* Ab thereon. Whether streptavidin-HRP was immobilized was confirmed by directly measuring the activity of HRP enzyme. Whether biotin-*Salmonella* Ab was immobilized was confirmed by alkaline phosphate-conjugated anti-rabbit immunoglobulin G antibody.

In this Experimental Example, a measurement device disposed in a dark room as shown in FIG. 34 was used. An LOC holder was disposed over a vibrator so that vibration could be applied during movement of particles. When an LOC was placed on the LOC holder, a magnet could be moved by a magnet, pulling wire below the LOC, and the wire was connected to an external syringe pump so that it could be pulled at a certain speed. A photodetector was disposed immediately above the detection chamber of the LOC so that it could detect light immediately the particles 200 moved.

The detection chamber 120 of the LOC was filled with Lumigen PS-atto, and a mixture of 10 µg of the capture particles 220, 10 µg of the labeling particles and a sample containing *Salmonella* bacteria was added to the sample chamber 110. The LOC was placed in a measurement device, and the magnet was moved from the sample chamber 110 to the detection chamber 120 at a speed of cm/min while vibration was applied. During movement of the magnet, the intensity of light was measured. As a result, as shown in FIG. 35, light started to be emitted from about 100 seconds after the start of movement of the magnet, and the intensity of light reached a constant value after 250 seconds. In addition, the final intensity of light was proportional to the number of *Salmonella* bacteria. From, the above results, it could be seen that bacteria could be detected using two kinds of particles, that is, magnetic capture particles 220 and non-magnetic labeling particles.

DESCRIPTION OF REFERENCE NUMERALS USED IN THE DRAWINGS

100: analyte detection device;
110: sample chamber; 111; sample inlet;
112: reactant chamber plug or buffer chamber plug;
113: reactant; 114: dried reactant;
115: solvent; 116: reactant solution;
120: detection chamber; 130: channel;
131: first connection passage; 132: second connection passage;
140: labeling chamber; 150: waste chamber;
160: reactant chamber; 170: fixing cover;
171: first protrusion or second protrusion;
200: particles;
210: analyte; 220: capture particles;
230: labeled receptor; 240: labeling capture particles;
250: labeling particles;
300: system for detecting analyte using gravity:
310: valve;
400: system for detecting analyte using centrifugal force;
410: disc; 420: detector;

440: valve; 450: valve;
451: valve body; 452: clamp;
500: system for detecting analyte using magnetic force;
510: force application unit; 520: filter.

The invention claimed is:

1. A method for detecting an analyte using an analyte detection device, the analyte detection device comprising: a sample chamber which contains a mixed solution of a sample containing the analyte and a reactant comprising capture particles and labeling particles; a detection chamber which contains a detection solution; and a channel located between the sample chamber and the detection chamber so as to prevent the mixed solution and the detection solution from mixing with each other; the method comprising the steps of:

mixing the reactant with the sample in the sample chamber to form a capture particle-analyte-labeling particle complex;

moving the capture particle-analyte-labeling particle complex to the detection chamber by a magnetic force application unit; and detecting the analyte in the detection chamber, wherein the capture particles are magnetic particles having immobilized thereon a primary receptor specific for the analyte, and the labeling particles are nonmagnetic particles which have immobilized thereon the primary receptor specific for the analyte and comprise a label, wherein the capture particle-analyte-labeling particle complex is moved by moving the magnetic force application unit from the sample chamber to the detection chamber in a state in which the magnetic force application unit is located on an outside of the analyte detection device, wherein the magnetic force application unit is a magnet.

2. A method for detecting an analyte using an analyte detection device, the analyte detection device comprising: a sample chamber which contains a mixed solution of a sample containing the analyte and a reactant comprising capture particles having immobilized thereon a primary receptor specific for the analyte and a labeled standard material having a label linked to a standard material; a detection chamber which contains a detection solution; and a channel located between the sample chamber and the detection chamber so as to prevent the mixed solution and the detection solution from mixing with each other; the method comprising the steps of:

mixing the reactant and the sample in the sample chamber to form a capture particle-analyte complex and a capture particle-labeled standard material complex;

moving the capture particle-analyte complex and the capture particle-labeled standard material complex to the detection chamber by a magnetic force application unit; and detecting the analyte in the detection chamber by use of the label linked to the labeled standard material, wherein the standard material is capable of binding to the primary receptor competitively with the analyte and the capture particles are magnetic particles having immobilized thereon a primary receptor specific for the analyte, wherein the capture particle-analyte complex and the capture particle-labeled standard material complex are moved by moving the magnetic force application unit from the sample chamber to the detection chamber in a state in which the magnetic force application unit is located on an outside of the analyte detection device, wherein the magnetic force application unit is a magnet.

3. A method for detecting an analyte using an analyte detection device, the analyte detection device comprising: a sample chamber which contains a mixed solution of a sample containing an analyte and reactants comprising capture particles having immobilized thereon a first receptor specific for the analyte and a labeled receptor having a label attached to a second receptor specific for the analyte; a detection chamber which contains a detection solution; and a channel located between the sample chamber and the detection chamber so as to prevent the mixed solution and the detection solution from mixing with each other; the method comprising the steps of:

mixing the reactants and the sample in the sample chamber to form a capture particle-analyte-labeled receptor complex;

moving the capture particle-analyte-labeled receptor complex to the detection chamber by a magnetic force application unit; and detecting the analyte using the label attached to the labeled receptor, wherein the first receptor and the second receptor are capable of binding non-competitively to different sites of the analyte and the capture particles are magnetic particles having immobilized thereon a primary receptor specific for the analyte, wherein the capture particle-analyte-labeled receptor complex is moved by moving the magnetic force application unit from the sample chamber to the detection chamber in a state in which the magnetic force application unit is located on an outside of the analyte detection device, wherein the magnetic force application unit is a magnet.

* * * * *